US012121422B2

(12) United States Patent
Chaffringeon

(10) Patent No.: US 12,121,422 B2
(45) Date of Patent: Oct. 22, 2024

(54) SWAB KIT FOR SAMPLING SPECIMENS FROM HUMANS OR ANIMALS, COMPRISING A SAMPLING CLOTH WOUND IN SPIRAL, AND PROCESS OF MANUFACTURING SUCH A SWAB KIT

(71) Applicant: UP BILLION FZE, Dubai (AE)

(72) Inventor: Bernard-Marie Chaffringeon, Pitesti (RO)

( * ) Notice: Subject to any disclaimer, the term of this patent is extended or adjusted under 35 U.S.C. 154(b) by 0 days.

(21) Appl. No.: 18/550,923

(22) PCT Filed: Oct. 20, 2021

(86) PCT No.: PCT/IB2021/059659
§ 371 (c)(1),
(2) Date: Sep. 15, 2023

(87) PCT Pub. No.: WO2022/195346
PCT Pub. Date: Sep. 22, 2022

(65) Prior Publication Data
US 2024/0033134 A1  Feb. 1, 2024

Related U.S. Application Data

(63) Continuation-in-part of application No. PCT/IB2021/052278, filed on Mar. 18, 2021.

(51) Int. Cl.
*A61F 13/38* (2006.01)
*A61B 10/00* (2006.01)
(Continued)

(52) U.S. Cl.
CPC ........ *A61F 13/385* (2013.01); *A61B 10/0045* (2013.01); *A61B 10/0291* (2013.01); *A61F 13/36* (2013.01)

(58) Field of Classification Search
CPC .... A61B 10/02; A61B 10/0291; A61F 13/385
See application file for complete search history.

(56) References Cited

U.S. PATENT DOCUMENTS

| 5,214,821 A | 6/1993 | Burrow |
| 5,928,176 A | 7/1999 | Nakatani |
(Continued)

FOREIGN PATENT DOCUMENTS

| CN | 205215271 U | 5/2016 |
| WO | 2020183225 | 9/2020 |

OTHER PUBLICATIONS https://www.sewsassy.com/LingerieProducts/nylon-tricot-fabric-wholesale.html (Year: 1987).*

*Primary Examiner* — Rene T Towa
*Assistant Examiner* — H. Q. Nguyen
(74) *Attorney, Agent, or Firm* — Law Office of Andrei D Popovici, PC

(57) ABSTRACT

The invention refers to a swab kit for sampling specimens from humans or animals, comprising a swab applicator (1) comprising a swab rod (2) having an extremity (E) and a sampling cloth (4) made of a low-absorbent flexible fabric, wherein the sampling cloth (4) is fixed to and wound, preferably in a spiral, in overlapping turns (T) around the swab rod (2), over a swab rod end region neighboring the extremity (E), in such a manner that at least an edge portion of the sampling cloth (4) overtops the extremity (E) by at least 1 mm when measured in a longitudinal direction of the swab rod (2).

9 Claims, 14 Drawing Sheets

(51) Int. Cl.
 *A61B 10/02* (2006.01)
 *A61F 13/36* (2006.01)

(56) References Cited

U.S. PATENT DOCUMENTS

| | | | |
|---|---|---|---|
| 9,173,779 B2 * | 11/2015 | Triva | A61B 10/0045 |
| 9,504,452 B2 * | 11/2016 | Triva | A61B 10/0096 |
| 2003/0108846 A1 | 6/2003 | Hoertsch | |
| 2013/0184684 A1 | 7/2013 | Yardley | |

* cited by examiner

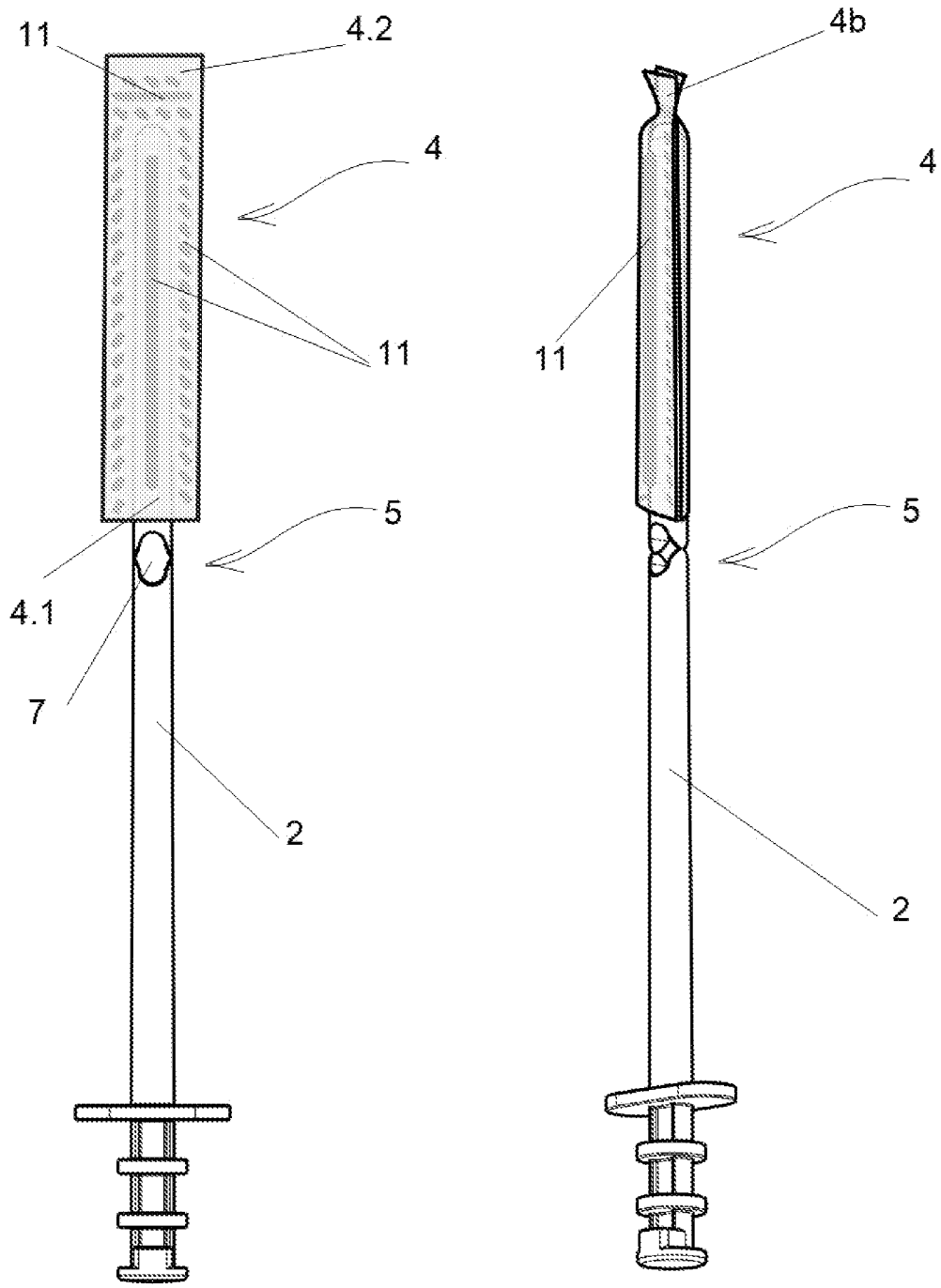

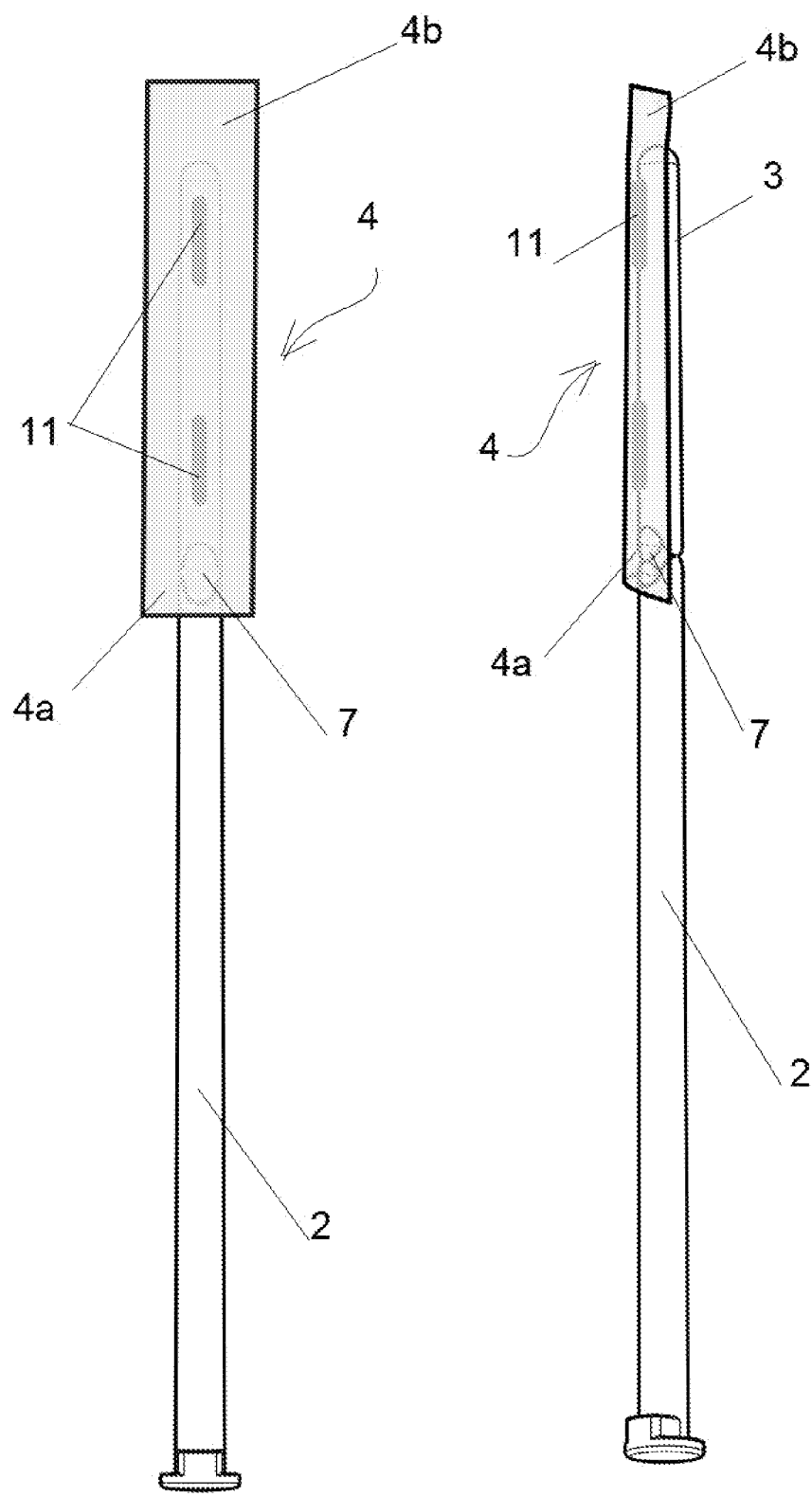

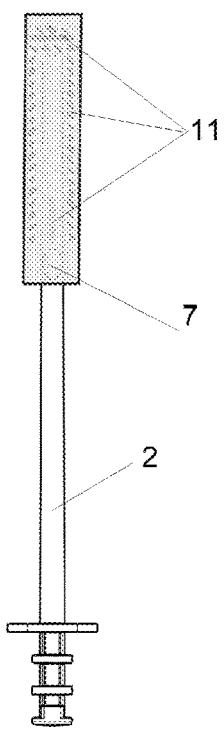
Fig. 9a
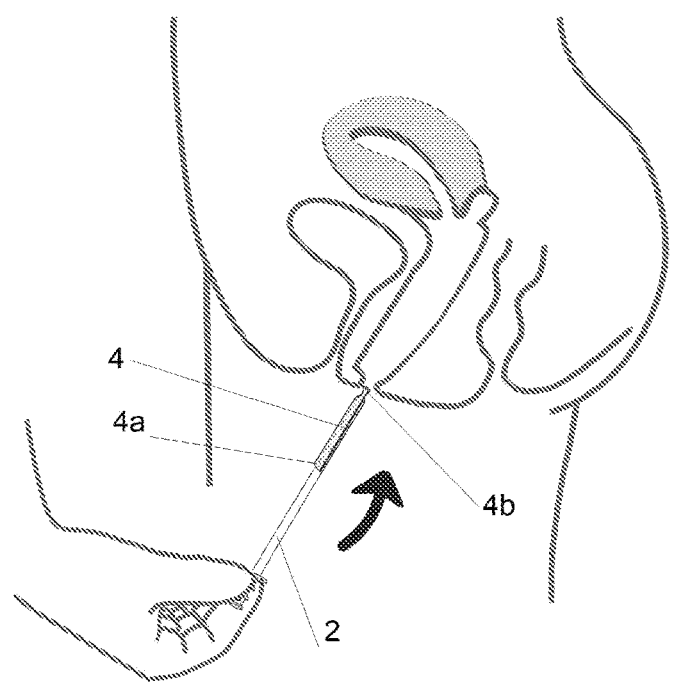
Fig. 9c
Fig. 9b
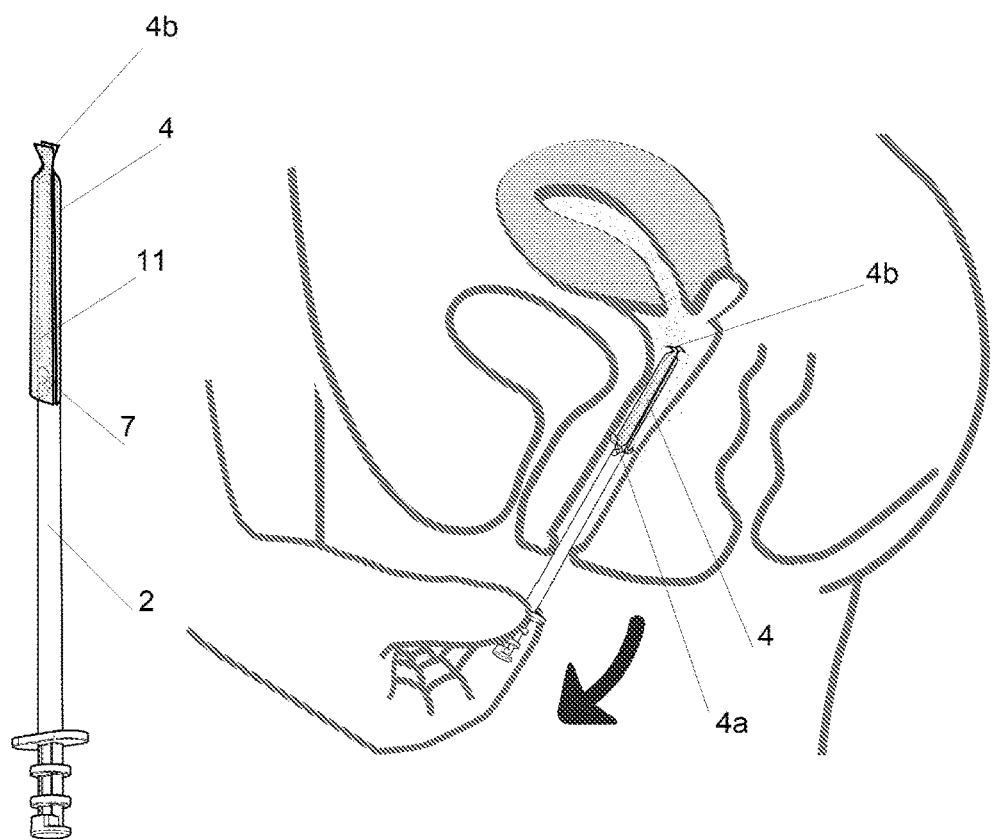
Fig. 9d

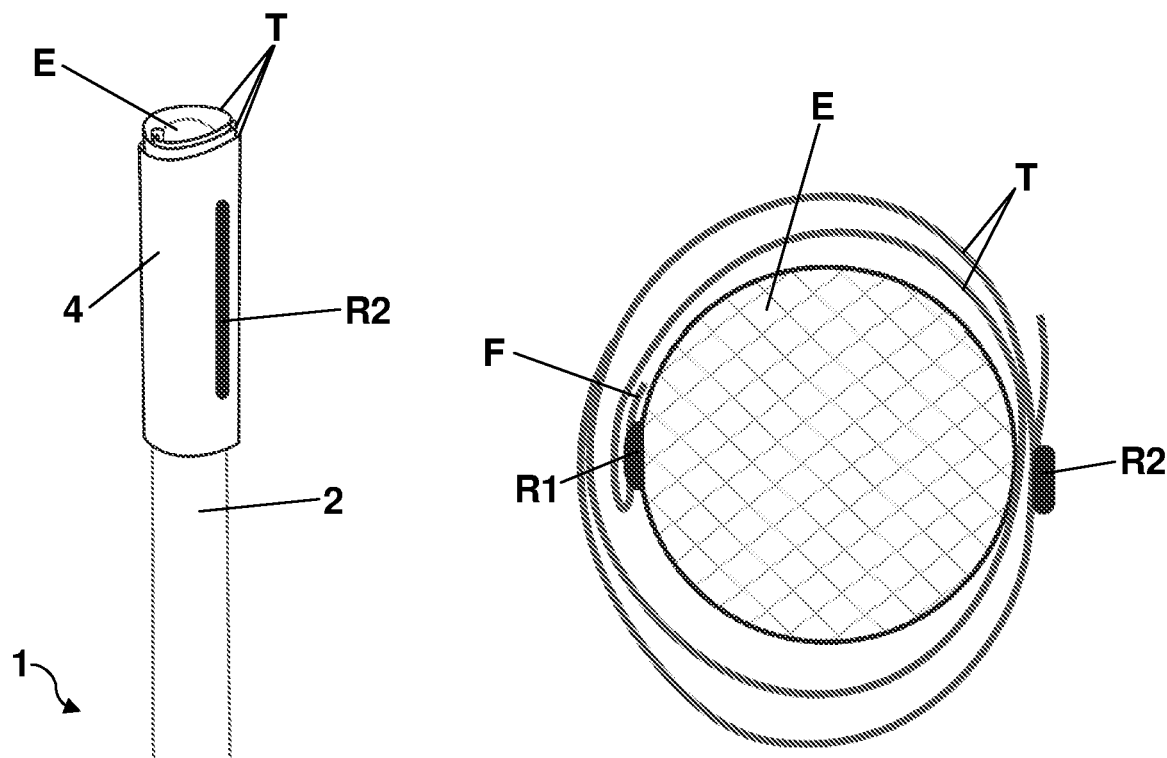
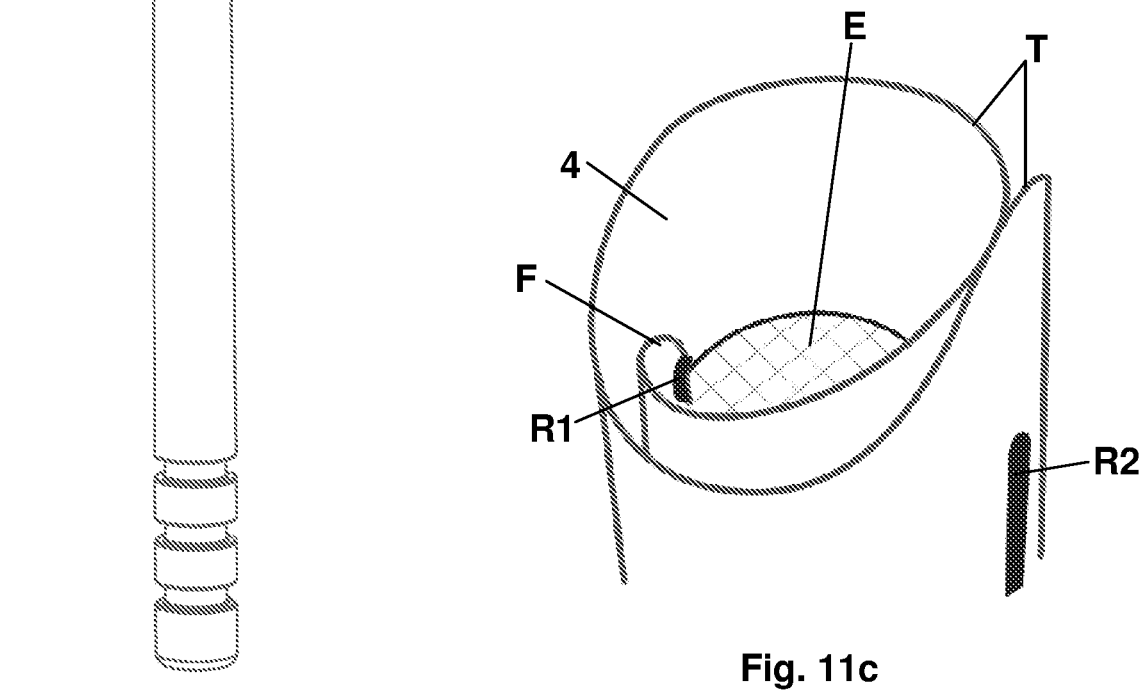
Fig. 11a
Fig. 11b
Fig. 11c

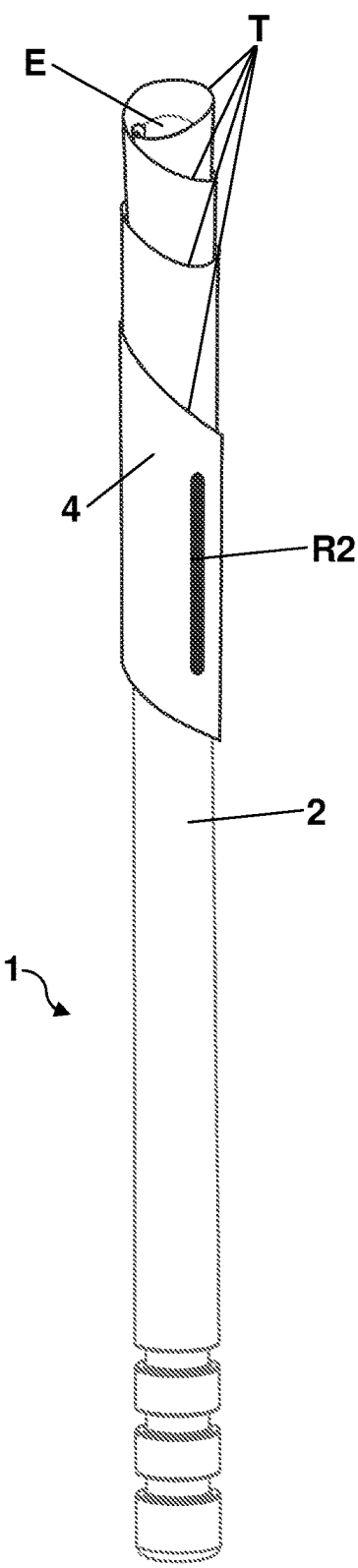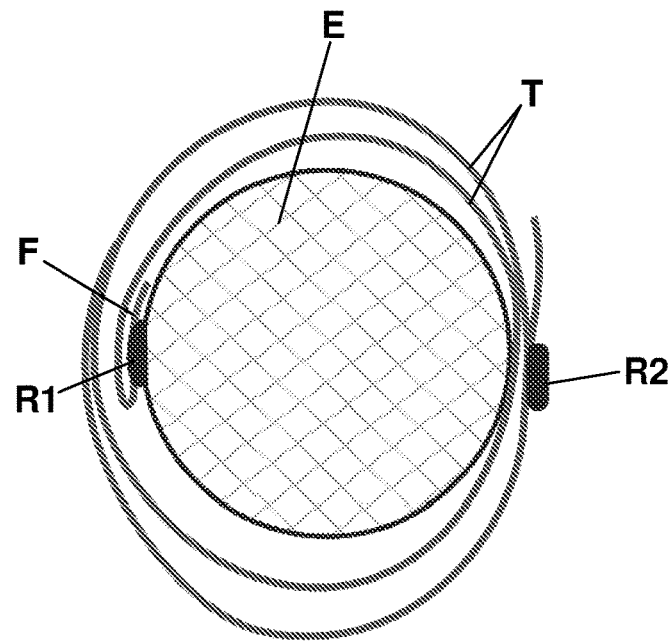
Fig. 12b
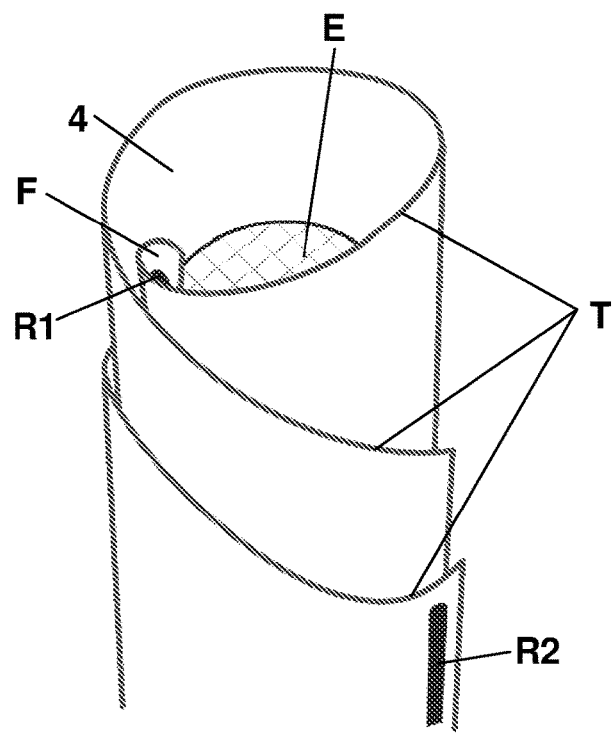
Fig. 12c
Fig. 12a

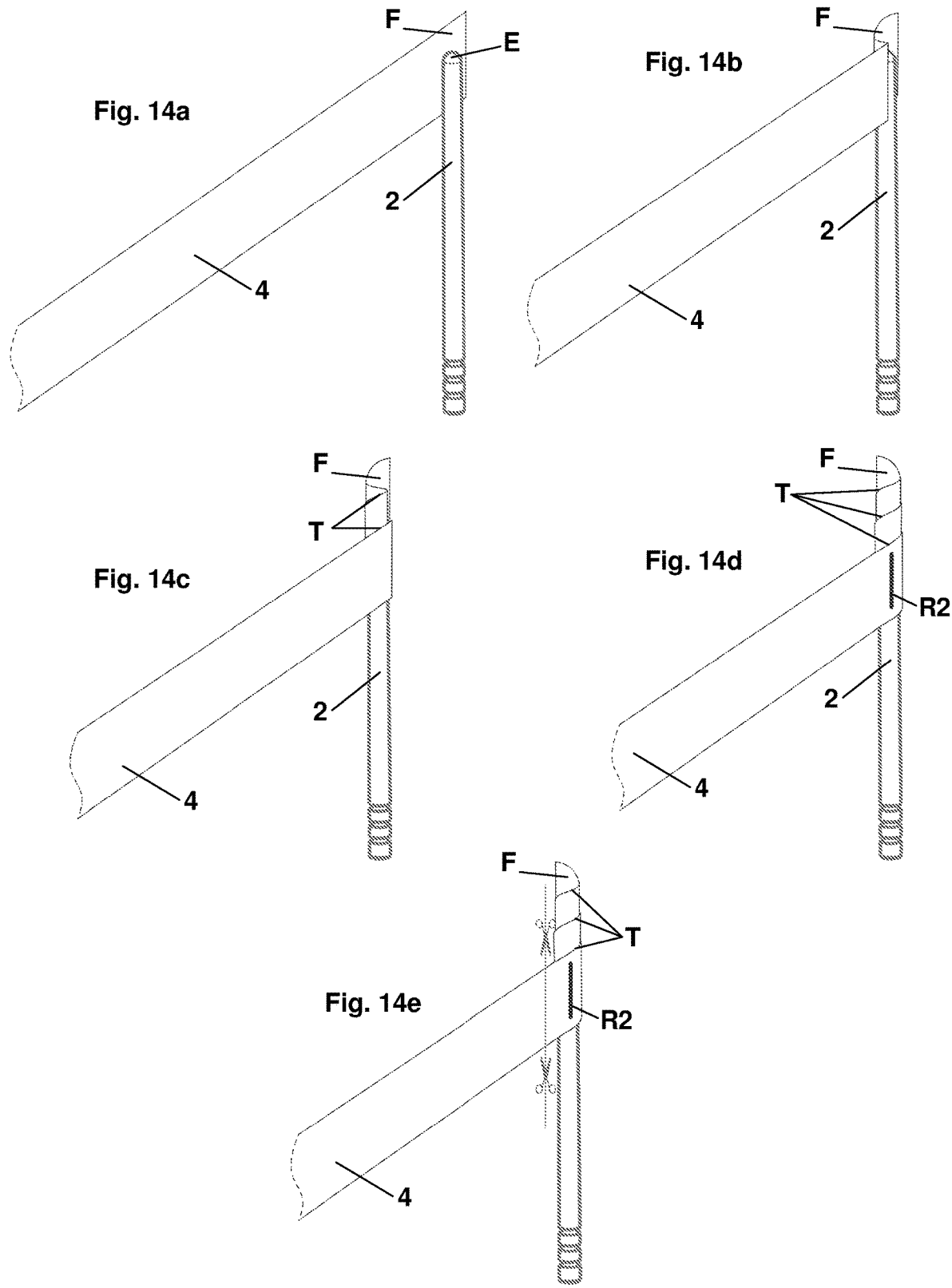

SWAB KIT FOR SAMPLING SPECIMENS FROM HUMANS OR ANIMALS, COMPRISING A SAMPLING CLOTH WOUND IN SPIRAL, AND PROCESS OF MANUFACTURING SUCH A SWAB KIT

The present application claims priority of the international application PCT/IB2021/052278 filed on Mar. 18, 2021. Paragraphs [0002] to [0012], [00015] to [0021], [0023] to [0068] and FIGS. 1÷10 from the present application are identical to those from the priority application.
The rest of the paragraphs and figures from the present application are newly introduced (they are not present in the priority application).

The present invention relates to the field of swab kits for sampling specimens from humans or animals bodily cavities. A swab kit comprises a swab applicator and a swab cloth. Sampling specimens are, for example, cells, cell residues, proteins, DNA, RNA. Human or animal bodily cavities are, for example, vaginal cavity, rectal cavity, oral cavity, nasal cavity.

BACKGROUND OF THE INVENTION

The swab sampling is the most commonly used and convenient sampling method during collection and transmittal of biological samples. Swab applicators are currently used with a sampling material such as cotton wool or fibrous material for sampling for specimens and/or culture material from human or animal bodily cavities such as the vaginal cavity, rectal cavity, oral or nasal cavity.

Conventional swab applicators include a swab rod made of wood or a plastic material, a handle and a swab or sampling head at an end of the swab rod, opposite the handle. The sampling material is wrapped on the swab head. Such applicators may be kept in a sterile package until they are to be used. These swab applicators have dimensions suitable to allow an easy insertion inside a specific bodily cavity of a human or animal. For this reason, the swab applicator has to be long enough to ensure a secure hold with the user's fingers during insertion/removal and at the same time to allow the grip area to remain outside of the bodily cavity during the sampling process.

Collecting specimens such as cytological, DNA, RNA, viruses such as the Coronavirus or HPV, and/or biologic samples for testing, study and diagnosis, especially for cervical cancer or STIs usually requires a complex examination and an often painful sampling made by a trained specialist (physician or nurse). Such samplings for testing for cervical cancers or STIs are traditionally performed on women by a gynecologist by inserting a speculum into the patient's vagina in a manner to expose the cervix of the uterus and then inserting a cervical scraper (with a swab or a brush) for sampling tissue from the endocervical canal and cervical os. The cervical scrapers are designed to scratch the tissue in order to take samples of tissue. Throughout this process, the woman must remain in a reclining (gynecological) position. Finally, the obtained specimen is applied directly on a glass slide, or placed into a recipient containing a liquid preservative in order to go through the analysis and evaluation steps. However, in about 30% of cases, unsatisfactory specimens are collected by this technique, leading to the need to repeat the procedure or to false or incomplete results.

In order to carry out a diagnostic test on a patient, the swab applicator is used to obtain a specimen or culture sample from the area to be tested, for example the patient's throat. Then, the trained specialist (physician or nurse) cuts the swab head of the swab applicator with scissors and puts it into a small container (for example a vial) which can be filled with a liquid preservative that can preserve the collected specimen or culture sample. The vial is then transported to the laboratory, where the contents thereof are tested.

A potential disadvantage with this known swab applicator for taking a culture sample test is that it is possible for the doctor or nurse who takes the test to contaminate the test sample by the handling of the swab applicator. The frequent use of scissors to cut the swabs may also bring in bacteria and thus affecting the test results.

Recent developments in this field have resulted in a breakable swab applicator which can easily break or separate the swab head from the swab rod after the sampling of a specimen, without using scissors.

CN204106055U Utility model application discloses a breakable cotton swab applicator which comprises a swab rod, a swab head provided at an end of the swab rod and the swab rod having at least one break groove, preferably adjacent to the cotton swab head. The break groove is an annular groove that is circumferentially opened along the swab rod. After the sampling is done, the swab applicator's head is placed into the open end of a vial and the testing personnel only need to press the swab rod to break the swab head from the swab rod and seal the vial to be sent to the testing laboratory. This can be done without using scissors. Additionally, two swab heads may be provided at each end of the swab rod and two break grooves may be provided near each of the two swab heads of the swab rod.

CN205215271U Utility model application discloses a breakable swab applicator which comprises a swab rod, a swab head provided at an end of the swab rod and an annular groove which facilitates the breaking of the swab head. The annular groove is preferably disposed near one end of the swab head. Another preferred embodiment of the swab applicator comprises a swab rod with a hollow structure, an auxiliary swab rod, a swab head and a break groove. One part of the swab head is disposed in the break groove as a fixed end and the other part of the swab head is used as a sampling swab head. The width of the break groove and the thickness of the swab head are equal to the inner diameter of the swab rod. The auxiliary swab rod is connected to the hollow swab rod. The diameter of the auxiliary swab rod is equal to the inner diameter of the swab rod such that the auxiliary swab rod can slide along the hollow structure of the swab rod without falling out. When the sampling is completed, the auxiliary swab rod is pushed up to push the swab head so that the swab head is detached from the break groove and left in the vial.

CN206818436U Utility model application discloses a breakable swab applicator which comprises a swab rod, a handle and a sampling head. The swab rod is provided with a plurality of easy-breaking concave grooves. In the longitudinal section, the easy-breaking concave groove has the shape of an inverted triangle and the inner side of the top end of the groove is positioned at the axial center of the swab rod. An anti-slip layer is provided on the outer side of each of the easy-breaking concave grooves which can ensure that the swab rod is firmly fixed on the edge of the vial and does not slide off. The easy-breaking concave grooves are opened on one side of the swab rod.

Thus, another disadvantage of the known swab applicators with a break groove opened to the outside of the swab rod is that it is easy to cause damage to the tissue of the sampled organ when inserting or removing the swab applicator into/out of the bodily cavity due to the sharp edges of the grooves.

Also, the known swab applicators with easy-breaking grooves have only one breaking point/surface. Therefore, a certain degree of stress is put on the trained specialist (physician or nurse) while using the known swab applicators. If the insertion force is increased above a certain level, the accidental breaking of the swab head inside the bodily cavity during the sampling process can occur, if not handled with caution.

Technical Problem

The object of the present invention is to eliminate the disadvantages presented above, by providing an inexpensive swab kit comprising an applicator and a sampling cloth, with improved precision rate and efficacy in sampling, and preserving specimens like cells, cell residues, DNA, RNA, proteins, viruses, bacteria, parasites, or fungi and/or other materials of interest from the bodily cavities of humans or animals without damaging the tissue of the sampled organ.

This aim is achieved by a swab kit and a swab kit manufacturing process as described below.

Definitions

By sampling it is meant a process of harvesting specimens wherein the sampling procedure can be performed by a professional, such as a doctor or a nurse, by an individual on him—or on herself, or by an individual on another individual without the assistance from a trained professional.

By specimen it is meant any cell, cell residue, DNA, RNA, protein, virus, bacterium, parasite, fungus and/or other material of interests.

A direction of insertion (x) of the swab applicator is defined, which is a longitudinal axis of the swab applicator and being oriented from the end of the swab applicator that remains outside the bodily cavity, called distal end of the swab applicator, to the end of the swab applicator that first contacts said cavity, called proximal end of the swab applicator. When looking in the direction of insertion, the top of the swab applicator or the upper part is represented by the extremity of the swab applicator that comprises its proximal point; that is the point that first contacts the bodily cavity. At the same time, the bottom of the swab applicator or the lower part is represented by the extremity of the swab applicator that comprises its distal end; that is the point of the swab applicator opposite to the proximal point, i.e. placed at the furthest distance from the proximal point on the insertion direction. Taking into account the above definitions, then lateral sides of the swab applicator will be the left and right extremities, considering the top and bottom as defined above.

The sampling cloth according to the invention is designed to be inserted into the bodily cavity of a human or animal, by means of the swab applicator. Thus, a direction of insertion of the sampling cloth is defined, which is a longitudinal axis of the sampling cloth and being oriented from the end of the sampling cloth that last enters the bodily cavity or remains outside the cavity, called distal end of the sampling cloth, to the end of the sampling cloth that first enters said bodily cavity, called proximal end of the sampling cloth. When looking in the direction of insertion, the top of the sampling cloth or the upper part is represented by the extremity of the sampling cloth that comprises its proximal point; that is the point that first enters the cavity. At the same time, the bottom of the sampling cloth or the lower part is represented by the extremity of the sampling cloth that comprises its distal end; that is the point of the sampling cloth opposite to the proximal point, i.e. placed at the furthest distance from the proximal point on the insertion direction. In some embodiments, part of the sampling cloth may protrude outside from the vaginal or rectal cavity. In such a situation, the bottom of the sampling cloth will also comprise such part of the sampling cloth. Taking into account the above definitions, then lateral sides of the sampling cloth will be the left and right extremities, considering the top and bottom as defined above.

The upper edge of the sampling cloth is the edge on the top of the sampling cloth while the lower edge of the sampling cloth is the edge situated on the bottom of the sampling cloth. According to the invention, "upper", "up" or "above" will refer to a first point or part situated closer to the top of the sampling cloth relative to a second point of reference, while the second point will be situated "lower", "down" or "below", respectively, to said first point or part.

According to the invention oriented upwards means oriented towards the top of the sampling cloth while oriented downwards means oriented towards the bottom of the sampling cloth.

The distance from the proximal end to the distal end of the sampling cloth defines the length of the sampling cloth.

The central longitudinal axis of the swab applicator or of the sampling cloth or of the swab head/rod or of any part of the swab applicator is defined as an imaginary line passing through the centroid of the cross sections along a longitudinal axis of the swab applicator/sampling cloth/swab head/swab rod . . . etc.

The longitudinal axis passes through the swab applicator or any part of the swab applicator from its proximal end to its distal end as defined above.

The central transverse axis of the swab applicator or of the sampling cloth or of the swab head/rod or of any part of the swab applicator is defined as an imaginary line passing through the centroid of the cross sections along a transverse axis of the swab applicator/sampling cloth/swab head/swab rod . . . etc.

The transverse axis passes through the swab applicator or any part of the swab applicator from left to right or from one lateral side to the other lateral side as defined above and it is always perpendicular to the longitudinal axis.

BRIEF DESCRIPTION OF THE DRAWINGS

Other objectives, advantages and characteristics of the invention shall be presented in the following description of the embodiments, which do not restrict the purpose and extent of this patent application, accompanied by drawings in which:

FIG. 6a depicts a front view of a swab kit according to an embodiment of the present invention wherein the through hole of the breakable section has the shape of an irregular oblong ring with two V-shaped sections connected by two bent sections and positioned in the proximity of the distal end of the sampling cloth wherein only one of the two sheets of fabric of the sampling cloth is visible; In this embodiment, the fastening means forming the long sides and the proximal end of the sampling area are spot welding rows and the fastening means that fix the sampling cloth to the swab head is a single straight row of continuous welding. Also, between the two spot welding rows at the proximal end of the sampling area is provided a single straight row of continuous welding;

FIG. 6b depicts a lateral view of a swab kit according to an embodiment of the present invention wherein the through hole of the breakable section has the shape of an irregular oblong ring with two V-shaped sections connected by two bent sections and positioned in the proximity of the distal end of the sampling cloth wherein the two sheets of fabric of the sampling cloth are visible and fastened to the swab head by a single straight row of continuous welding and to each other on the lateral sides by spot welding rows;

FIG. 7a depicts a front view of a swab kit according to an embodiment of the present invention wherein the through hole of the breakable section has the shape of an irregular oblong ring with two V-shaped sections connected by two bent sections and positioned completely under the distal end of the sampling cloth wherein only one of the two sheets of fabric of the sampling cloth is visible; In this embodiment, the fastening means that fix the sampling cloth to the swab head are two straight rows of continuous welding;

FIG. 7b depicts a lateral view of a swab kit according to an embodiment of the present invention wherein the through hole of the breakable section has the shape of an irregular oblong ring with two V-shaped sections connected by two bent sections and positioned completely under the distal end of the sampling cloth wherein only one sheet of fabric of the sampling cloth is provided and fastened to the swab head by two straight rows of continuous welding;

FIG. 9a depicts a front view of a swab kit according to an embodiment of the present invention wherein the through hole of the breakable section has the shape of an irregular oblong ring with two V-shaped sections connected by two bent sections and is positioned completely under the distal end of the sampling cloth wherein only one of the two sheets of fabric of the sampling cloth is visible; In this embodiment, the fastening means forming part of the long sides and the proximal margin of the sampling area are spot welding rows and between the two spot welding rows at the proximal margin of the sampling area is provided a single straight row of continuous welding. The sampling cloth is fastened to the swab head, proximally to the breaking section, by a single straight row of continuous welding. At the distal margin of the sampling cloth are two distal flaps extending from the distal end of the sampling cloth to the fastening means;

FIG. 9b depicts a lateral/side view of a swab kit according to an embodiment of the present invention wherein the through hole of the breakable section has the shape of an irregular oblong ring with two V-shaped sections connected by two bent sections and is positioned completely under the distal end of the sampling cloth wherein two sheets of fabric of the sampling cloth are visible; The fastening means are placed as described in FIG. 9a. At the proximal margin of the sampling cloth are two proximal flaps extending from the fastening means to the proximal end of the sampling cloth and at the distal margin of the sampling cloth are two distal flaps extending from the distal end of the sampling cloth to the fastening means;

FIGS. 9c and 9d represent sequential views of some steps of a method for sampling according to the invention, with a swab kit according to an embodiment wherein the sampling cloth is provided with proximal flaps and distal flaps and is inserted and then removed inside/outside a vaginal cavity. FIG. 9c depicts the closed state of the proximal and distal flaps upon insertion of the swab kit into the vaginal cavity and FIG. 9d depicts the open state of the proximal and distal flaps upon removal of the swab kit from the vaginal cavity;

FIGS. 11a-11c show a further embodiment of a swab kit according to the invention, wherein the sampling cloth is wound around the swab rod;

FIGS. 12a-12c show a further embodiment of a swab kit according to the invention, wherein the sampling cloth is wound in spiral around the swab rod;

FIGS. 14a-14e show the process steps of manufacturing the swab kit embodiment of FIGS. 12a-12c.

DETAILED DESCRIPTION OF THE INVENTION

Breakable swab applicator

Figure 1:
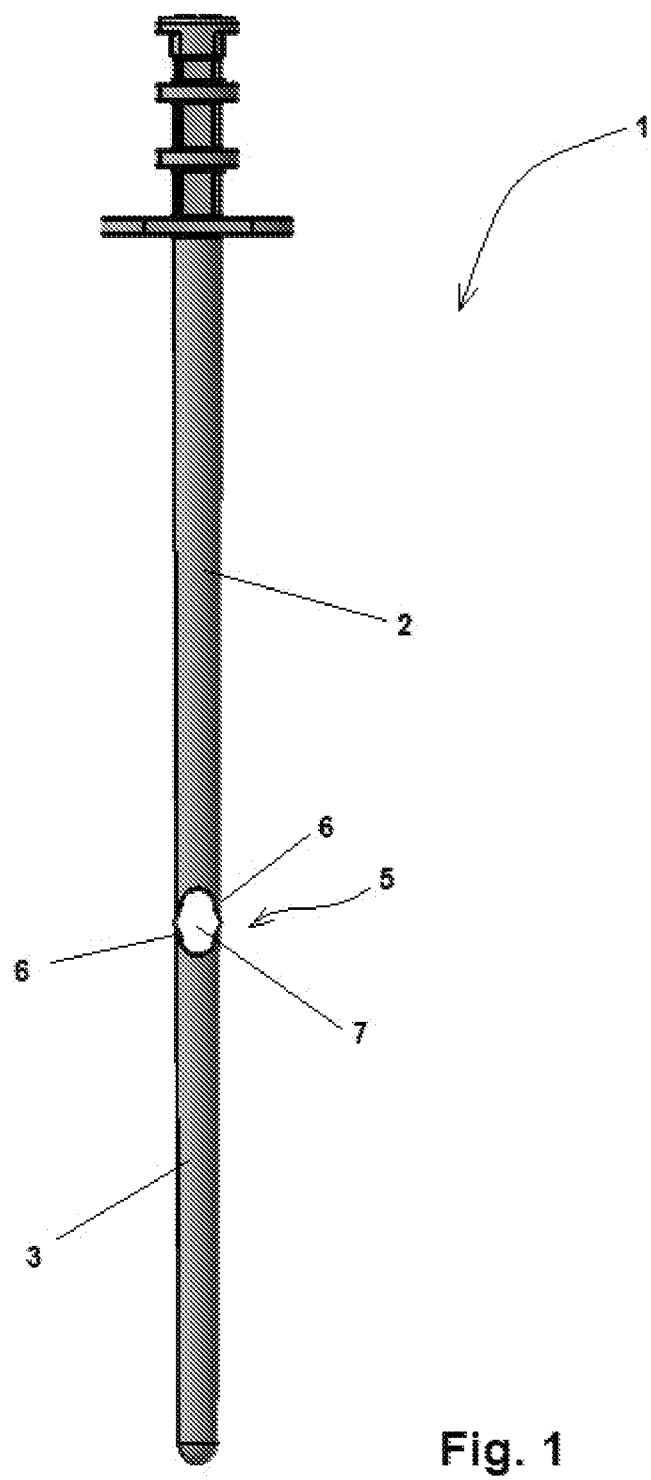
FIG. 1 depicts a front view of a swab applicator according to an embodiment of the present invention wherein the through hole of the breakable section has the shape of an irregular oblong ring with two V-shaped sections connected by two bent sections.
Figure 2:
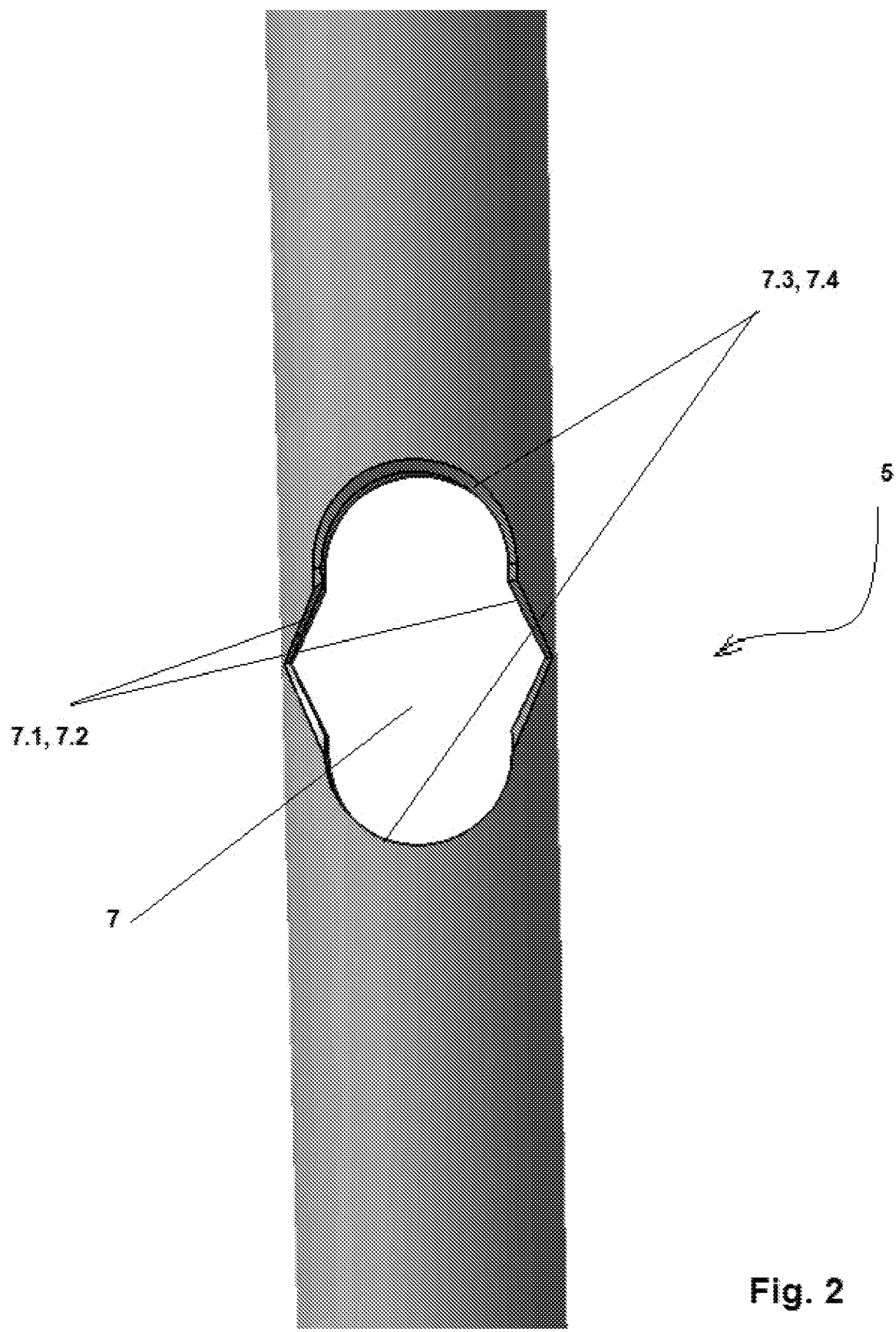
FIG. 2 depicts a detailed front view of the through hole of the breakable section having the shape of an irregular oblong ring with two V-shaped sections connected by two bent sections.
Figure 3:
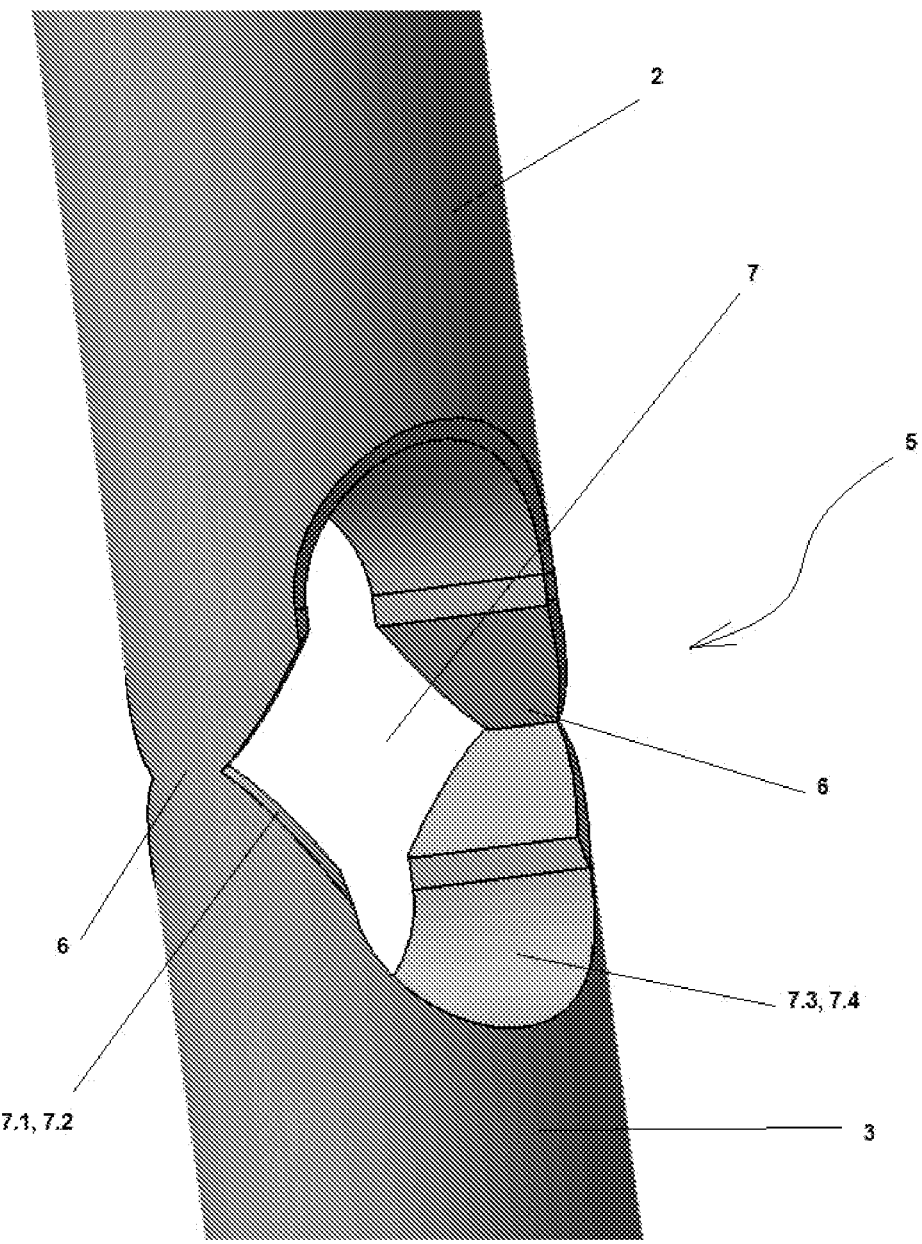
FIG. 3 depicts a detailed lateral/side view of the through hole of the breakable section having the shape of an irregular oblong ring with two V-shaped sections connected by two bent sections.
Figure 4A:
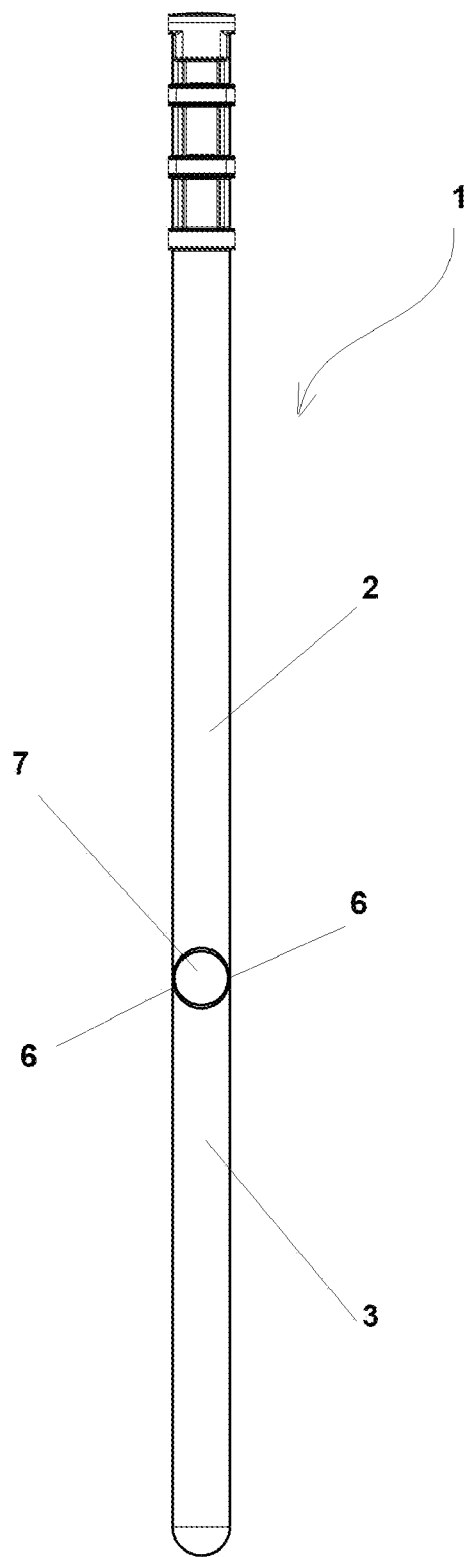
FIGS. 4a and 4b depict a detailed front (FIG. 4a) and lateral/side (FIG. 4b) view of the through hole of the breakable section having a cylindrical shape.
Figure 4B:
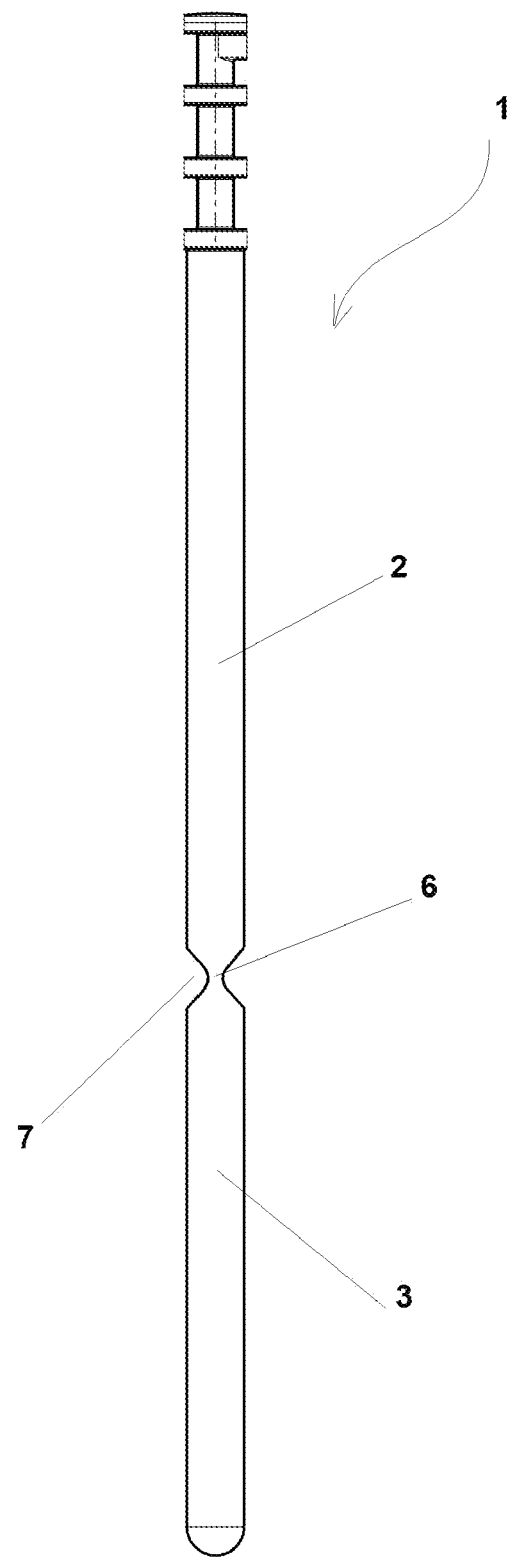
Figure 5:
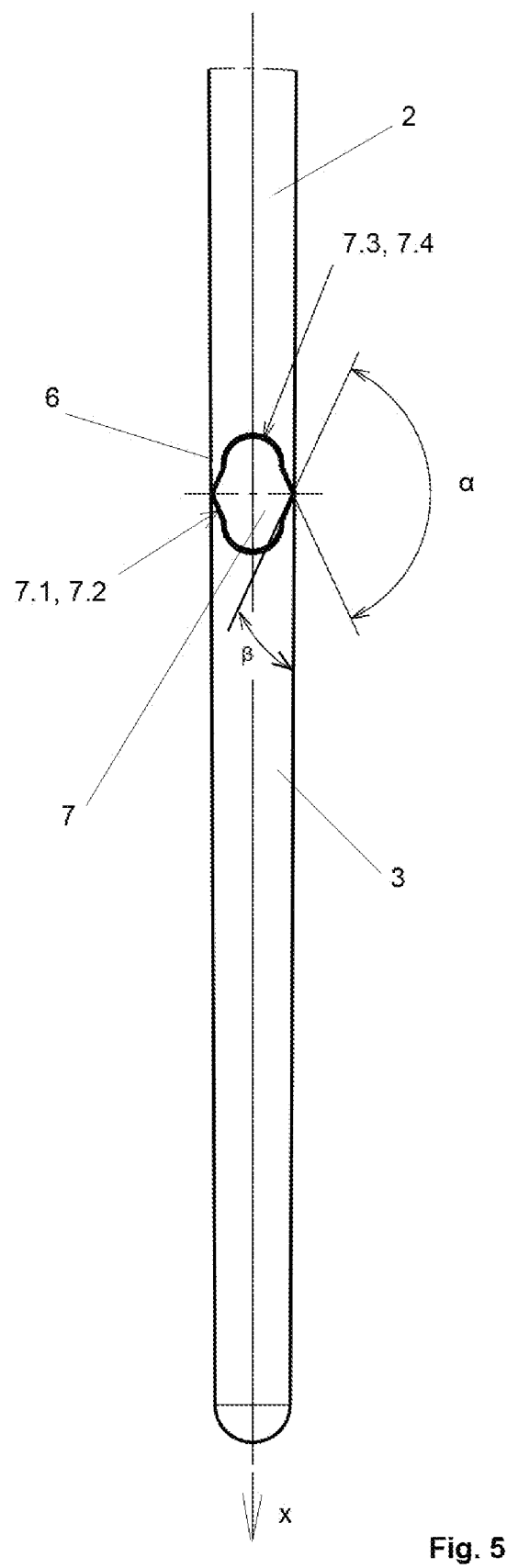
FIG. 5 depicts a front longitudinal cross-section through the swab applicator according to a preferred embodiment of the present invention wherein the through hole of the breakable section has the shape of an irregular oblong ring with two V-shaped sections connected by two bent sections.

The FIGS. 1-10 present a swab applicator 1 for use with a sampling cloth 4 as described in claim 1, comprising a swab rod 2 and an elongated swab head 3 which is disposed at an end of the swab rod 2. The swab rod and the swab head are connected to one another at a breakable section 5, wherein the distal end of the swab head and the proximal end of the swab rod are connected to said breakable section 5. In a preferred embodiment of the invention, the swab rod and the swab head are connected to one another such that their central longitudinal axis corresponds at the breakable section 5.

The swab rod 2 and the swab head 3 have a shape, and dimensions adapted to those of the bodily cavity for which the swab applicator 1 is intended and the strength necessary to be able to push the sampling cloth 4 inside the bodily cavity of a human or animal without breaking during insertion and/or removal and breakable upon application of a breaking force to the swab rod 2. The swab applicator 1 is disposable (one use-only). The swab applicator 1 may be made of any suitable material, such as plastic. Preferably, the swab applicator is made of Polyester (polyethylene terephthalate (PET)), ABS (Acrylonitrile Butadiene Styrene) or low density polyethylene PE-LD, which have low production costs, good flexibility, low weight, recyclable and can be easily molded or thermoformed.

The swab applicator 1 may be releasably inserted, centered or off centre, in a dedicated pocket of the sampling cloth 4. Preferably, the width of said pocket is 2-6 mm bigger than the diameter of the swab applicator 1, for a smooth insertion and removal. Optionally, the swab applicator 1 may have a gripping area, for gripping during insertion and removal of the swab applicator from the bodily cavity. Said gripping area may have an adherent surface, or may be shaped so that it can be easily and firmly held by the human hand. For example, the swab applicator may have, along the gripping area, a series of recesses or elevations.

The swab rod 2 and the swab head 3 may be made in the form of a solid or hollow body which can be: a cylindrical body, an elongated rectangular prism or any suitable shape preferably with smooth, curved or rounded lateral sides/ends or extremities, preferably chamfered or with a radius within a range of about 0.1×45° to about 0.3×45°, which facilitates insertion/removal of the swab applicator and avoids damages to the tissue during the sampling process. For human use, such a swab applicator 1 may have for example, a length (the height of the applicator) of about 120 mm to about 150 mm and a width (diameter of the applicator) below 10 mm. In all embodiments, the length of the swab applicator 1 is adapted to the bodily cavity in which it is desired to be inserted. Thus, in case it is used for insertion into the vaginal cavity, the length of the swab applicator 1 is preferably maximum 150 mm.

In all embodiments, the width and cross-section of the swab applicator 1 are adapted to the bodily cavity in which it is meant to be inserted and are proportional to the swab applicator's dimensions. The proximal end of the swab applicator 1 which is also the proximal end of the elongated swab head 3 may have a smooth, rounded shape which facilitates insertion of the swab applicator 1 into the bodily cavity and/or into a dedicated pocket of the sampling cloth 4. Preferably, the radius of the proximal end of the swab head 3 or swab applicator 1, in a front longitudinal cross-section is within a range of about 1.5 mm to about 2.5 mm.

The breakable section 5 comprises two connection walls 6 which are integrally formed with the swab rod 2 and the swab head 3. The breakable section 5 has also a through hole 7 which extends transversally on the central longitudinally axis of the breakable section 5 or of the swab applicator 1. The through hole 7 is delimited by the connection walls 6, at its left and right extremities, as seen in the direction of insertion (x) defined above. The through hole 7 may be a circular, oval, ellipse or any shape of through hole which serves the purpose of the present invention.

In a preferred embodiment (see FIGS. 1-3 and 5), the through hole 7 has in a front longitudinal cross-section through the swab applicator 1, the shape of an irregular oblong ring. This special shape of the through hole 7 comprises two V-shaped sections 7.1, 7.2 connected by two bent sections 7.3, 7.4.

The "V" shape has two equal or approximately equal sides of an isosceles triangle and a tip or apex where the two sides are connected. The two equal or approximately equal sides are called the legs of the "V" shape. The angle measured between the two sides or legs, at the interior of the imaginary isosceles triangle, is called the V opening angle a or the apex angle a. Each of the two V-shaped sections 7.1, 7.2 has a V opening angle a within a range of about 120° to about 136°, preferably of about 130°. Each of the V-shaped section is symmetrically placed with respect to the centre of the breakable section 5 in a longitudinal plane through each connection wall 6 and with their V-shaped opening facing each other. The apex of each of the V-shaped section is placed at the centre of the breakable section 5 on a connection wall 6. The legs of the V-shaped sections 7.1, 7.2 are connected by the bent sections 7.3, 7.4 to form the shape of an irregular oblong ring. The bent sections 7.3, 7.4 may have an arc shape, a V shape or any other suitable shape. Preferably, the radius of the bent sections 7.3, 7.4 is within a range of about 0.9 mm to about 2.35 mm. In another preferred embodiment, the V-shaped sections 7.1, 7.2 are preferably identical and/or said bent sections 7.3, 7.4 are preferably identical in size and/or shape.

Each connection wall 6 has two lateral side faces that start tapering in the proximity of the breakable section 5 towards the central transverse axis of the breakable section 5 resulting in a pre-determined minimum length and thickness of each of the two connection walls 6 proximally to the central transverse axis of the breakable section 5. The angle measured between a longitudinal axis of a connection wall 6 and a lateral side face of said wall 6 in the proximity of said minimum length is called the angle of taper 13 and is preferably chosen within a range of about 22° to about 30°, more preferably about 25°.

The pre-determined minimum length and thickness of each of the two connection walls 6 proximally to the central transverse axis of the breakable section is chosen such that the two connection walls 6 are strong enough to hold the swab rod 2 and the elongated swab head 3 together during normal use of said swab applicator 1 (i.e. during insertion and/or removal of the swab applicator), and breakable upon application of a breaking force to the swab rod 2. The two connection walls 6 are integrally formed with the swab head and swab rod and provide two breaking points/surfaces proximally to the central transverse axis of the breakable section 5, instead of only one breaking point/surface as compared to the known breakable swab applicators. This ensures that the swab applicator 1 can be inserted and removed in/out of the bodily cavity without accidentally breaking the swab head 3 during insertion or removal of the swab applicator 1. Also, the fact that the two connection walls 6 are integrally formed with the swab head 3 and the swab rod 2 ensures that the swab applicator 1 can be inserted/removed into/out of the bodily cavity easily, painlessly and without causing damages to the tissue of the sampled organ.

The pre-determined minimum length is preferably within a range of about 0.65 mm to about 1.3 mm and the pre-determined minimum thickness of each connection wall 6 is preferably within a range of about 0.15 mm to about 0.37 mm. The pre-determined minimum length and thickness of each of the two connection walls 6 proximally to the central transverse axis of the breakable section 5 is chosen according to the maximum diameter or maximum width of the swab applicator 1. The ratio between the minimum length of a connection wall 6 and the maximum diameter of the swab applicator 1 is preferably between 1:2 and 1:8 and the ratio between the minimum thickness of a connection wall 6 and the maximum diameter of the swab applicator 1 is preferably between 1:8 and 1:33.

In a preferred embodiment the maximum diameter of the swab rod and of the swab head is of 3 mm. The through hole 7 has a circular shape in a cross section with a diameter of 2.7 mm. The minimum length of a connection wall 6 is of 0.94 mm and the minimum thickness of a connection wall 6 is of 0.15 mm. The center of the breakable section 5 is positioned at a distance of 50.5 mm from the distal end of the swab applicator 1 to its proximal end. The swab applicator 1 has a total length of 135 mm measured between its distal and proximal ends.

In another preferred embodiment the maximum diameter of the swab rod and of the swab head is of 3 mm. The through hole 7 has the shape of an irregular oblong ring, as described above, with the distance between the apexes of the two V-shaped sections of 2.7 mm. The angle a of the V-shaped opening measures 136°. The two V-shaped sections 7.1, 7.2 are identical regarding their shape and size. The maximum distance between the two legs of a V-shaped section is of 2.24 mm. The bent sections 7.3, 7.4 are identical regarding their shape and size. The shape of the bent sections is circular in a cross section, with a radius of 0.9 mm. The minimum length of a connection wall 6 is of 1.11 mm and the minimum thickness of a connection wall 6 is of 0.15 mm. The center of the breakable section 5 is positioned at a distance of 50.5 mm from the distal end of the swab applicator 1 to its proximal end and the breakable section 5 has a total length of 4.8 mm measured in the direction of insertion (x). The swab applicator 1 has a total length of 135 mm measured between its distal and proximal ends.

In another preferred embodiment the maximum diameter of the swab rod and of the swab head is of 5 mm. The through hole 7 has a circular shape in a cross section with a diameter of 4.7 mm. The minimum length of a connection wall 6 is of 1.3 mm and the minimum thickness of a connection wall 6 is of 0.15 mm. The center of the breakable section 5 is positioned at a distance of 50.5 mm from the distal end of the swab applicator 1 to its proximal end. The swab applicator 1 has a total length of 135 mm measured between its distal and proximal ends.

In another preferred embodiment the maximum diameter of the swab rod and of the swab head is of 5 mm. The through hole 7 has the shape of an irregular oblong ring, as described above, with the distance between the apexes of the two V-shaped sections of 4.7 mm. The angle a of the V-shaped opening measures 120°. The two V-shaped sections 7.1, 7.2 are identical regarding their shape and size. The maximum distance between the two legs of a V-shaped section is of 2.94 mm. The bent sections 7.3, 7.4 are identical regarding their shape and size. The shape of the bent sections is circular in a cross section, with a radius of 1.5 mm. The minimum length of a connection wall 6 is of 0.65 mm and the minimum thickness of a connection wall 6 is of 0.15 mm. The center of the breakable section 5 is positioned at a distance of 50.5 mm from the distal end of the swab applicator 1 to its proximal end and the breakable section 5 has a total length of 6 mm measured in the direction of insertion (x). The swab applicator 1 has a total length of 135 mm measured between its distal and proximal ends.

In the preferred embodiments where the through hole 7 has a circular, oval or ellipse shape in a cross section, the flexibility of the swab applicator 1 is increased because the minimum pre-determined length of the connection walls 6 proximally to the central transverse axis of the breakable section 5 is larger compared to the through hole 7 with the shape of an irregular oblong ring.

In the latter case, the minimum pre-determined length of the connection walls 6 proximally to the central transverse axis of the breakable section 5 is smaller, preferably between 0.65 mm and 1.11 mm. The V-shaped sections 7.1, 7.2 provide a better control of the breaking of the swab head 3 after removal of the swab applicator 1. Also, if the maximum diameter of the swab head and of the swab rod is smaller, for example 3 mm, the resistance to breakage is higher and thus the control of the breaking of the swab head 3 after removal is better.

The skilled person will be able to calculate the appropriate resistance to breakage of the connection walls 6 proximally to the central transverse axis of the breakable section 5 by using the common general knowledge in the field of invention, e.g. taking into consideration the size of the applicator at the breakable section, the length and thickness of the connection walls, etc. To break the connection walls 6 in order to separate the swab rod 2 from the swab head 3, a breaking force must be applied to the swab rod 2 after removal of the swab applicator 1 from the bodily cavity. The breaking force can be a rotating force or lateral, linear force acting on the swab rod 2.

The swab applicator 1 is preferably made by injection molding, which is a manufacturing process for producing parts by injecting molten material into a mould, or mold. Moulds can be of a single cavity or multiple cavities. In multiple cavity moulds, each cavity can be identical and form the same parts/products or can be unique and form multiple different geometries during a single cycle. Preferably, for the manufacturing of the swab applicator 1, a multi-cavity mould is used because we will achieve more products faster such that we will have a shorter lead time per batch, more efficient use of the cycle time and lower product price.

Swab kit

The swab kit according to the invention comprises a swab applicator 1, as described above, and a sampling cloth 4 designed to be inserted into the bodily cavity. Optionally, the swab kit may comprise a sealable recipient 9 such as a vial for storing and transporting said sampling cloth 4 to a diagnosis facility such as a laboratory. The swab kit may further comprise instructions for its use and/or labeling means.

The swab kits known in the art for sampling cells, nucleic acids or specimens for culture or microbiologic assays are designed to reproduce, as closely as possible, the traditional sampling process that takes place, for example, in the gynecologist's office. As such, they are concerned to protect the swab applicator and sampling material from coming into contact with the bodily cavity walls and secretions (by keeping it inside a tube during insertion and extraction) and give advice on how to avoid the risk of contamination, i.e. of having the sampling material touch any of the part of the vagina than the one targeted. They work on the assumption that cells and DNA from the uterus may be sampled only by collecting precisely from the cervical area, and they sample specimens from only a reduced area of the bodily cavity. Also, they work by a complicated methodology which must be correctly performed in order to obtain specimens of a quality comparable to those taken by a gynecologist. A key element of this methodology consists in attempting to contact the sampling material (small brush or sponge) directly with the cervical os, manually move the sampling material in a circular movement and then immediately retracting the sampling material/swab applicator and extracting the swab applicator.

By contrast, the use of the sampling cloth 4 together with the swab applicator 1 according to the present invention is much simpler and less traumatic. The entire experience is physically and mentally comfortable, while at the same time rendering high quality results. The sampling cloth 4 can be introduced into the bodily cavity easily, painlessly and in privacy. Said sampling cloth 4 is easy to wear and may be comfortably left inside the bodily cavity for a period of time before it is extracted and housed in a separate recipient 9. Contrary to the above mentioned teachings of the prior art stating that the sampling must be made precisely in the cervical area, we have found that the use of the sampling cloth 4 succeeds every time in collecting cells and nucleic acids from the uterus. Actually, the specimens collected by using the sampling cloth 4 of the invention contain significantly more material of interest such as cells, DNA, proteins, resulting in a more complete and accurate detection, than specimens taken by a doctor or a nurse in the traditional manner. These surprising findings have been proven by rigorous essays. These essays show that, by using the sampling cloth 4 of the invention, up to 10 times more HPV DNA has been collected from each individual than by using the traditional sampling process. Also, more strains of HPV have been diagnosed for each tested subject from the samples collected with the swab kit, resulting in a more correct and complete diagnosis of the HPV infections than from samples collected by a trained professional using the traditional sampling method in a medical facility. Additionally, by getting into contact with virtually the entire surface of the bodily cavity, as well as the external tissues, every potential specimen of interest (such as cells, nucleic acids, proteins, viruses, bacteria, parasites or fungi) may be caught by said sampling cloth 4 and released when needed.

The sampling cloth 4 of the invention may also be used for collecting samples for detecting bacteria (such as *Neisseria gonorrhea, Chlamidia trachomatix, Mycolpasma hominis, Mycoplasma urealyticum, Syphilis, Streptococcus*), parasites (such as *Trichomonas vaginalis*) or fungi (such as *Candida albicans*).

The sampling cloth 4 according to the invention is designed to be inserted into the bodily cavity of a human or animal, by means of the swab applicator 1. The sampling cloth 4 is made of a material suitable to be introduced into a bodily cavity such as the vagina or rectum. Thus, the sampling cloth 4 can be comfortably fitted inside the bodily cavity. Said suitable material will be flexible, by which it is to be understood a material that will bend and unbend to follow the shape of for example, the vagina or rectum. Also, a suitable material will be preferably atraumatic, by which it is to be understood a material that may be put into contact with or made to slide over or wipe a surface of a body membrane such as the vaginal or rectal mucosa without causing any injury or discomfort such as irritation, pain etc., preferably a fabric with a soft carded smooth surface. The use of a sampling cloth 4 made of such a flexible, atraumatic material has the advantage that avoids the irritation of the bodily cavity, pain and discomfort during the insertion that are usually associated with the use of the swab kits from the state of the art. Preferably, when the sampling cloth 4 is introduced into the vagina with the aid of the swab applicator 1, the sampling cloth 4 above and around said applicator 1 will protect the vaginal mucosa from direct contact with the hard material of the swab applicator 1.

Advantageously, a suitable material for the sampling cloth 4 is a material that can catch specimens from the bodily cavity and preferably retain said specimens on its surface, while at the same time being able to subsequently easily release said specimens so that they can be analyzed. Therefore, the sampling cloth 4 has advantageously a surface coming into contact with the bodily cavity, but with little or no absorbency, so that only a small amount of the specimens are absorbed into the fabric of the sampling cloth 4. According to the invention, the absorbency should be less than 3.5 g/g, preferably less than 3 g/g, more preferably less than 2 g/g measured using the Syngina protocol for measuring the absorbency of tampons. For example, an absorbency of 3.5 g/g means that 3.5 grams of liquid are absorbed per 1 gram of material.

Preferably, the sampling cloth 4 is made of a fabric having low thickness. A sampling cloth having low thickness will be able to catch the specimens on its surface, but it will not, or only minimally, transfer, collect and retain them in its depth. Such a sampling cloth has the advantage that, unlike a sponge or a tampon, it will not retain inside the collected specimens (cells, proteins, DNA, etc.) during the analysis and evaluation steps. Instead, the sampling cloth 4 will easily liberate the specimens from the sampling cloth, so the final quantity of specimens to be analyzed is maximized, which raises the precision rate (accuracy) of the sampling test. The thickness of the sampling cloth 4 should be of 3 mm or less, preferably 2 mm or less, more preferably 1 mm or less, even more preferably 0.6 mm or less, which means a thickness much smaller compared to a normal tampon. Advantageously, the material of the sampling cloth 4 has a basis-weight of approximately 60 $g/m^2$.

The material of the sampling cloth, suitable to be comfortably inserted into a bodily cavity, may be chosen from the group of a woven or non-woven textile, for example made of synthetic fibers (such as polyester, polypropylene, polyethylene, polyamide, polyacetate, polyvinyl acetate), semi-synthetic fibers (such as viscose, modal, lyocell), plant fibers (such as cotton), animal fibers (such as silk), or combinations thereof. In a preferred embodiment, the material is biodegradable, thus reducing the impact on the environment. Preferably, the material is a non-woven textile made of synthetic fibers, since such materials are atraumatic and have the desired low absorbency. Also, such products may have low production costs.

In a preferred embodiment, the material is also thermofusible, so that it may be welded to the exterior surface of the elongated swab head 3 and/or the lateral sides and/or top of the sampling cloth 4 may be welded to each other so that the sampling cloth 4 can be removably attached to the elongated swab head 3. Welding is a fabrication process that joins materials, by using high heat to melt the parts together and allowing them to cool, causing fusion.

In a more preferred embodiment, the sampling cloth 4 is made of a non woven fabric with a soft carded smooth surface comprising a non-woven polyethylene/polyester bicomponent. Preferably, such material has the following properties:
- average basis weight (mass per unit area), measured with WSP 130.1 Test method, of around 59.20 $g/m^2$,
- average tensile strength MD, representing the force per unit width which is required to rupture a sample orientated in the machine direction, measured with a Test method following WSP 110.4 using a sample width of 25.4 mm (1 inch), a clamp distance of 127 mm (5 inch) and a speed of 500 mm/min (19.7 inch/min), of around 48.86 N/inch
- average elongation at F-max MD, representing the relative increase in length at the maximum force applied on a sample orientated in the machine direction, measured with a Test method following WSP 110.4 using a sample width of 25.4 mm (1 inch), a clamp distance of 127 mm (5 inch) and a speed of 500 mm/min (19.7 inch/min), of around 38.40%.

In a preferred embodiment, the sampling cloth 4 according to the invention may have a region having a rougher surface than the rest of the sampling cloth (such as more roughly checkered organic cotton, linen or burlap), preferably placed so that it is most likely to reach and, by scratching the tissue, collect samples from a targeted area of the bodily cavity. For example, in order to collect samples from the cervical os, the rougher fabric can be placed at the top of the sampling cloth 4. The rougher fabric may, for example, be attached to the fabric of the sampling cloth by any suitable means such as gluing, welding, sewing, etc., or it may be integral part of the sampling cloth. A sampling cloth 4 having such a region with a rougher surface will be able to collect, in less time, specimens from the targeted area.

In a preferred embodiment, the sampling cloth 4 according to the invention is suitable to be inserted into the vaginal or rectal cavity of a human or animal. Thus, the person skilled in the art will understand to choose the dimensions of the sampling cloth 4 adapted to the dimensions of the bodily cavity where it is to be inserted.

The vagina and rectum are open cavities in the form of fibro-muscular tubes with walls that are easily distensible. The vagina is in the form of a tube having at the extremities an external opening (the vaginal opening) and an internal opening (communicating with the uterus). The rectum is in the form of a tube having at the extremities an external opening (the anus) and an internal opening (communicating with the large intestine); near the external opening it has a dilated portion, the rectal ampulla, where the sampling cloth 4 according to the invention is meant to be housed. The external openings of the vagina and rectum are substantially circular. The width (diameter) of the tubes (vagina and rectum) varies throughout their length, with the minimum width being at the external opening of the bodily cavity. For example, the human adult vagina or rectum at rest has, at the external opening, a width of about 2.5 cm.

Whatever the shape of the sampling cloth when outside the bodily cavity, due to the fact that it is made of a flexible fabric, when inserted into the bodily cavity by pushing it through the substantially circular external opening, the sampling cloth will collapse, e.g. deform, fold, strangle and/or twist to pass through the external opening and then will unfold to roughly follow the shape of the cavity. Therefore, the dimensions of the sampling cloth for inserting into the human vaginal or rectal cavities will be chosen such that, in said collapsed position, the maximum width of the sampling cloth will be of less than 2.5 cm, so that it can be comfortably inserted into the bodily cavity.

In a preferred embodiment, when using a sampling cloth 4 of a substantially rectangular shape, the width of said rectangle may be chosen, for example, to be between 2 cm and 6 cm.

When inserted into the bodily cavity, which means after the sampling cloth 4 has been pushed inside the bodily cavity by means of the swab applicator 1; the sampling cloth 4 will preferably take a shape having the proximal end closest to the internal opening of the bodily cavity and the distal end closest to the external opening of the bodily cavity, and will occupy a roughly tubular space. Thus, the skilled person will be able to shape/choose the dimensions of the sampling cloth 4 so that when inserted into the bodily cavity, the sampling cloth will preferably have a length for example up to the maximum length of the vagina or of the rectal ampulla.

Figure 8A:
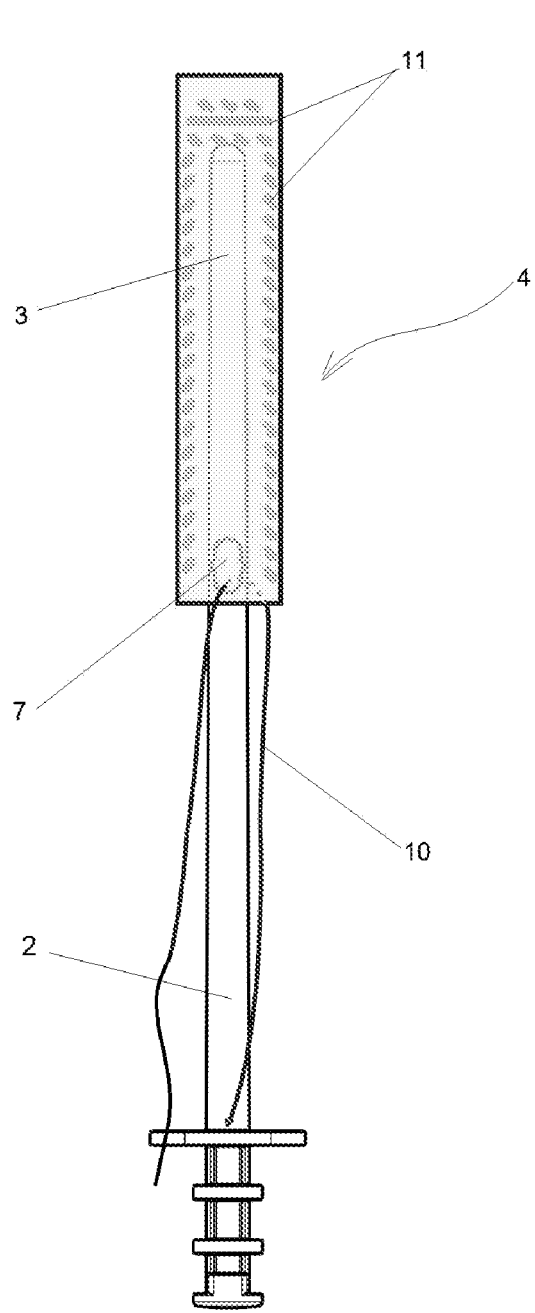
FIG. 8a depicts a front view of a swab kit according to an embodiment of the present invention wherein the through hole of the breakable section has the shape of an irregular oblong ring with two V-shaped sections connected by two bent sections and positioned completely under the distal end of the sampling cloth wherein only one of the two sheets of fabric of the sampling cloth is visible; In this embodiment, the fastening means forming the long sides and the proximal end of the sampling area are spot welding rows and between the two spot welding rows at the proximal end of the sampling area is provided a single straight row of continuous welding; The swab kit comprises also attachment means in the form of a yarn with one end fixed to the distal end of the swab rod in the proximity of the gripping means and the other end of the yarn is free and passed through the sampling cloth and through the through hole.
Figure 8B:
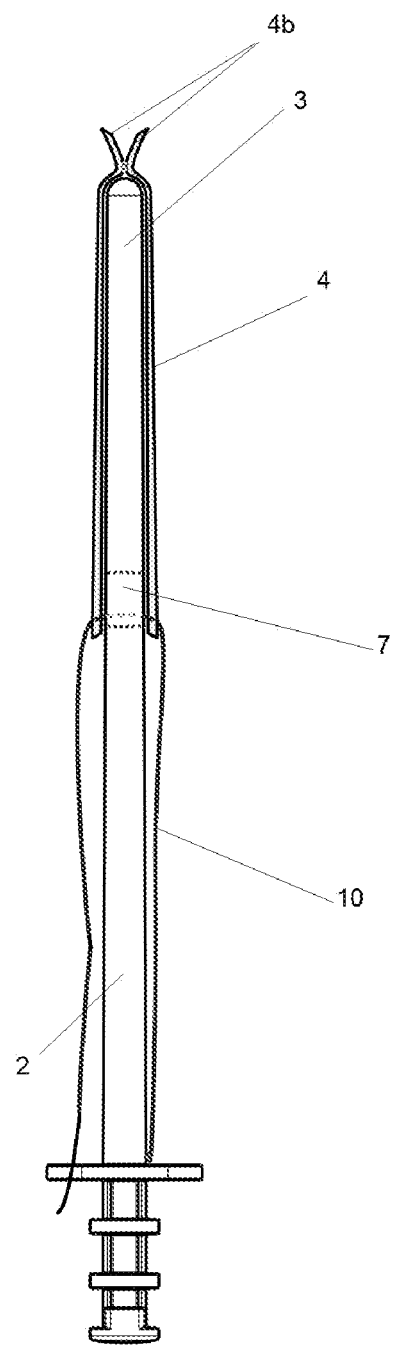
FIG. 8b depicts a lateral view of a swab kit according to an embodiment of the present invention wherein the through hole of the breakable section has the shape of an irregular oblong ring with two V-shaped sections connected by two bent sections and positioned completely under the distal end of the sampling cloth wherein the two sheets of fabric of the sampling cloth are visible; The swab kit comprises also attachment means in the form of a yarn with one end fixed to the distal end of the swab rod in the proximity of the gripping means and the other end of the yarn is free and passed through the one sheet of fabric of the sampling cloth, through the through hole and through the other sheet of fabric of the sampling cloth. At the proximal margin of the sampling cloth are two proximal flaps extending from the fastening means to the proximal end of the sampling cloth.
Figures 10A, 10B, 10C, 10D:
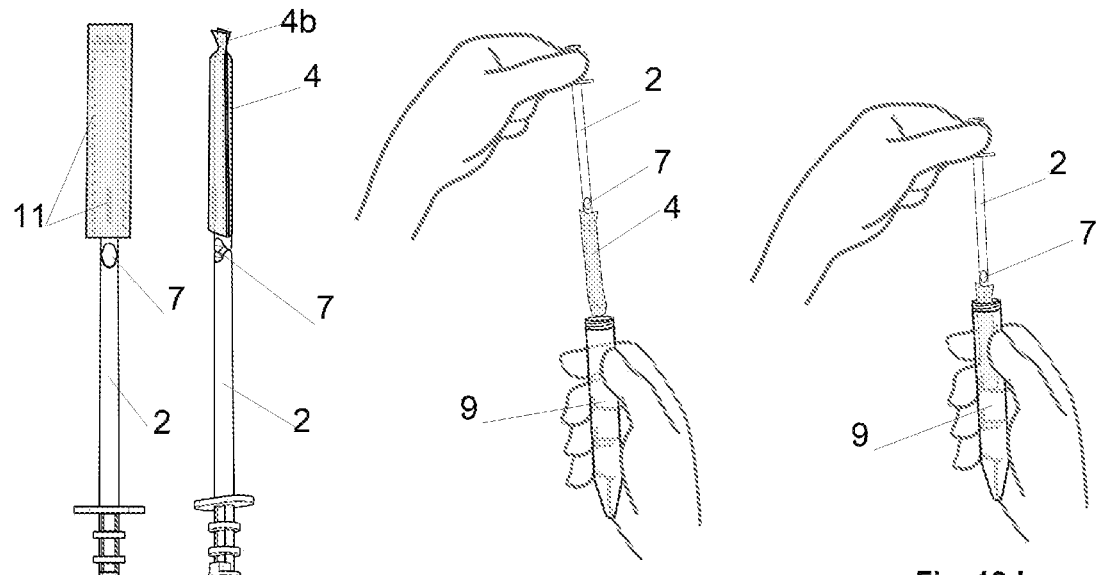
FIG. 10a depicts a front view of a swab kit according to an embodiment of the present invention wherein the through hole of the breakable section has the shape of an irregular oblong ring with two V-shaped sections connected by two bent sections and is positioned proximally to the distal end of the sampling cloth wherein only one of the two sheets of fabric of the sampling cloth is visible; In this embodiment, the fastening means forming the long sides and the proximal end of the sampling area are spot welding rows and between the two spot welding rows at the proximal end of the sampling area is provided a single straight row of continuous welding; The sampling cloth is fastened to the swab head, proximally to the breaking section, by a single straight row of continuous welding.
FIG. 10b depicts a lateral/side view of a swab kit according to an embodiment of the present invention wherein the through hole of the breakable section has the shape of an irregular oblong ring with two V-shaped sections connected by two bent sections and is positioned proximally to the distal end of the sampling cloth, wherein the two sheets of fabric of the sampling cloth are visible; In this embodiment, the fastening means forming the long sides and the proximal end of the sampling area are spot welding rows. The sampling cloth is fastened to the swab head, proximally to the breaking section, by a single straight row of continuous welding. At the proximal margin of the sampling cloth are two proximal flaps extending from the fastening means to the proximal end of the sampling cloth.
FIGS. 10c-10h show the embodiment of a swab kit after removal from the bodily cavity and views of the steps for breaking the swab applicator in order to detach the swab head with the sampling cloth from the swab rod and placing the swab head and the sampling cloth within a sealable recipient, and sealing said recipient.
Figure 10E:
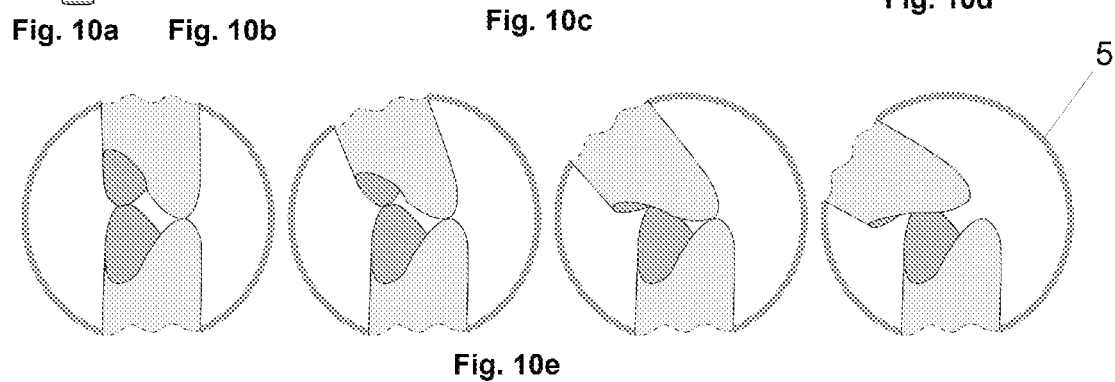
Figures 10F, 10G, 10H:
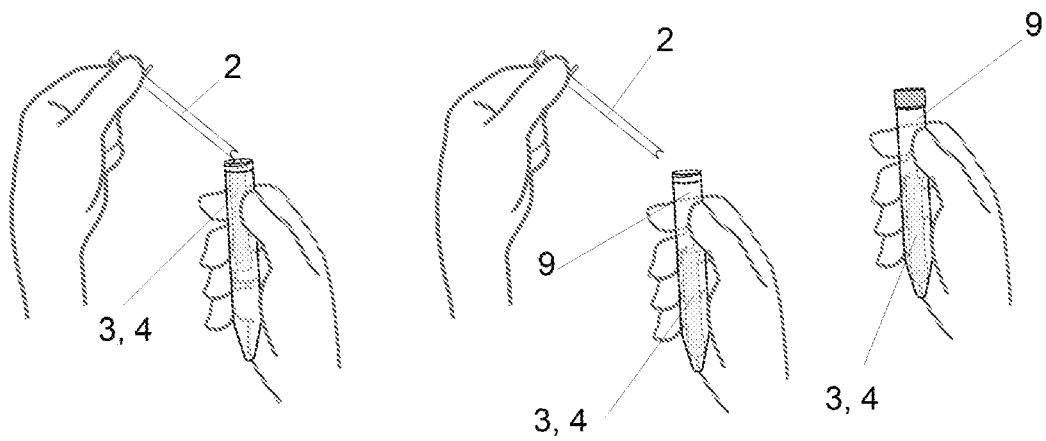

In a preferred embodiment, the length of the sampling cloth 4 after insertion into the bodily cavity is equal or slightly less than the length of said bodily cavity, so that specimens from virtually all the surface of the cavity may be sampled. In another embodiment, the sampling cloth 4 may have a length greater than the maximum length of the bodily cavity, so that part of the sampling cloth protrudes outside of the bodily cavity, in order to collect specimens from the area outside the cavity (such as vulva or anal orifice). Preferably, the distal end of the sampling cloth 4 may comprise attachment means 10, preferably one or more strings, such as threads or cords. In FIGS. 8a-8b, these attachment means 10 may preferably have a minimum length which is twice the length of the swab rod 2. One end of an attachment means 10 is preferably fixed to the distal end of the swab rod 2 and the other end of the attachment means 10 is preferably free and passed through the distal end of the sampling cloth 4 and through the through hole 7 such that during insertion of the swab applicator 1, the loose or free end of the attachment means 10 is gripped by the therapist or the nurse while using the swab applicator 1. After removal of the swab applicator 1 from the bodily cavity, the swab head 3 is detached from the swab rod 2 as described above and the free end of the attachment means 10 is released such that the swab head 3 together with the sampling cloth 4 are safely placed inside the sealable recipient 9 or vial to be sent to the laboratory. The attachment means 10 may be made of any material which does not tear when a force necessary to extract the sampling cloth 4 from the bodily cavity is applied thereon. Preferably, rupture resistance of such means is above 50 N. Also, the attachment means 10 are preferably made from materials which are not potentially toxic to humans or animals and to the environment. Such a preferred means of attachment 10 is a cotton yarn having a metric yarns number Nm of 16/4. Cotton is preferred because it is a natural, non-toxic fiber, comfortable to wear, resists static electricity build-up, is a moderately strong fibre and hypoallergenic. The means of attachment 10 may be attached to the sampling cloth 4 in any suitable way known in the art that would allow a good fixation, without detaching from the sampling cloth 4 during use or removal, such as by welding, sewing, pasting, stapling, buttoning, knotting or gluing.

For example, the length of the human adult vagina at rest varies from about 5 to about 14 cm, and the length of the human adult rectal ampulla varies from about 4 to about 6 cm. The skilled person will preferably choose the dimensions of the sampling cloth 4 for completely inserting in the vagina of a human so that, when inserted, the sampling cloth will have the length approximately equal or slightly less than the human vagina so that it can collect specimens from all parts of the vagina. Therefore, the skilled person will choose in this case a sampling cloth with a length of less than 14 cm, such as about 12 cm, about 10 cm, about 8 cm or less, preferably of about 10 cm.

For insertion in the human rectum the sampling cloth will be smaller, in order to stay in the rectal ampulla, for example having a length of less than 5 cm, preferably less than 3.5 cm.

The sampling cloth 4 can be made of at least one sheet of fabric having any suitable shape; preferably it may have, for example, a substantially rectangular, square, trapezoidal, parallelepipedic, oval or circular shape.

In a preferred embodiment (see FIGS. 6*b*, 8*b*, 9*b*, 10*b*), the sampling cloth 4 of the swab kit of the invention is substantially in the form of two sheets of fabric, each having a proximal margin situated at the proximal end of the swab head 3, a distal margin situated at the distal end of the swab head 3, and two lateral margins. Embodiments wherein the swab kit comprises two sheets of fabric are preferred because the method of producing the device from two sheets of fabric is simple and fast. These two sheets of fabric are preferably welded together, preferably on at least one side (top and/or bottom and/or lateral side) of the sheets of fabric and/or welded to the exterior surface or surfaces of the elongated swab head 3 along its longitudinal axis such that the surfaces of both sheets of fabric will come into direct contact with the bodily cavity, thus maximizing the contact surface where specimens are collected. Said sheets of fabric are preferably fastened to each other by welding or other fastening means 11 such as continuous welding lines, spot welding rows, sewing lines, and/or glue lines, which form the short side and the two long sides of the sampling cloth 4. In preferred embodiments, the fastening means 11, forming the short side of the sampling cloth 4, are made of two or more rows of welding spots and/or lines of continuous welding. For example, said short side of the sampling cloth may be made of two rows of welding spots and a line of continuous welding between the two rows. A fastening means 11 at the short side made of two or more rows and/or lines of welding is more resistant to the force of pushing of the swab applicator 1.

Such a sampling cloth will also allow for an easier release of the collected specimens (cells, proteins, DNA, etc.) from the sampling cloth 4 during the analysis and evaluation steps.

Also, in another preferred embodiment of the present invention (see FIGS. 7*a* and 7*b*), the sampling cloth 4 is shaped substantially in the form of a single sheet of fabric welded on a single exterior surface of the elongated swab head 3 of the swab applicator 1 along its longitudinal axis. Such a sampling cloth is efficient, as a sterilization process is easy to be conducted in one step only.

In a preferred embodiment, as shown in FIGS. 9*a* and 9*b*, the sampling cloth comprises at least one sheet of fabric, preferably two sheets of fabric, each having a proximal margin situated toward a proximal end of the swab head 3, and a distal margin situated toward a distal end of the swab head 3. Said sheets are fastened to each other by at least a fastening means 11 such as a continuous welding line, spot welding row, sewing line, and/or glue line situated at a distance of about 1 mm to 10 mm, such as 1 mm to 3 mm, 1 mm to 5 mm, 1 mm to 8 mm from the proximal margins of said sheets. Preferably, the swab kit comprises two sheets of fabric, each having a proximal margin situated at a proximal end of the swab head 3, a distal margin situated at a distal end of the swab head 3, wherein said sheets are fastened to each other by fastening means 11 such as continuous welding lines, spot welding lines, sewing lines, and/or glue lines to form a pouch having:
  an open end,
  a short side opposed to the open end and situated toward the proximal end of the swab head 3, and
  two lateral sides,
wherein said short side of the pouch is situated at a distance of about 1 mm to 10 mm, such as 1 mm to 3 mm, 1 mm to 5 mm, 1 mm to 8 mm from the proximal margins of said sheets.

Because said fastening means 11 is situated at a distance such as 1 mm to 10 mm from the proximal margins of the two sheets, the two sheets of fabric form, toward the proximal end of the swab head 3, two proximal flaps 4*b*, representing the sections of said two sheets extending from the fastening means 11, such as the short side of the pouch, to the proximal margins of each sheet. The two flaps 4*b* can be symmetrical, meaning that they have similar shapes and dimensions, or asymmetrical, meaning they can have shapes and dimensions different from each other. As mentioned, said two proximal flaps 4*b* are fixed to each other by the fastening means 11 along the short side of the pouch, and have each a free margin opposite the short side of the pouch that is also the proximal margin of the respective sheet of fabric. The two proximal flaps 4*b* can transition from a closed state, wherein their two free margins touch or are very close to each other, to an open state, wherein their two free margins get away from each other (see FIGS. 9*c*, 9*d*). Said proximal flaps 4*b* each has an inner face, which is the surface of the flap positioned toward the other flap when in closed state, and an opposite outer face, which is the surface of the flaps positioned toward the exterior of the sampling cloth 4 when in closed state. A sampling cloth 4 provided with such proximal flaps 4*b* can efficiently sample specimens, because, during insertion of the swab kit into the bodily cavity, the proximal flaps 4*b* transition to said open state, by the friction with the walls of the bodily cavity. This allows the specimens to be collected mainly on the inner faces, which are often positioned in the bodily cavity, when the swab kit is fully inserted, at the most important area for sampling, which is usually in the vicinity of the internal opening of the bodily cavity. During removal from the bodily cavity, the proximal flaps 4b transition back to the closed state, thus catching the specimens between the flaps, on their inner faces. This ensures that a sufficient amount of specimens are successfully sampled and kept on the inner faces of the flaps, which are not lost because only the external faces and rest of the sampling cloth 4 are wiped due to friction with the walls of the bodily cavity during removal.

In another preferred embodiment, the sampling cloth of the swab kit (see FIGS. 9a-9d) may comprise at least one sheet of fabric, having a proximal margin situated at a proximal end of the swab head 3, a distal margin, preferably situated at a distal end of the swab head 3. Even more preferred, the sampling cloth comprises two sheets of fabric, wherein said sheets are fastened to each other by fastening means 11 such as continuous welding lines, spot welding lines, sewing lines, and/or glue lines. In both cases, the sheets of fabric are also fastened to said swab head 3, for example on its longitudinal axis, by fastening means situated at a distance of about 1 mm to 10 mm, such as 3 mm to 8 mm or 4 mm to 6 mm from the proximal margin of the at least one sheet. The distal end side may be fastened at a distance of about 3 mm to 10 mm, preferably 3 mm to 8 mm or even more preferably, 4 to 6 mm from the distal margin of the at least one sheet .

Because said fastening means 11 is situated at a distance as specified above, from the proximal margins of the two sheets and at a distance as specified above from the distal margins of the one or two sheets, the two sheets of fabric form, toward the proximal end of the swab head 3, two proximal flaps 4b, representing the sections of said two sheets extending from the fastening means 11, and the one or two sheets of fabric form, toward the distal end of the swab head 3, one or two distal flaps 4a, representing the sections of said two sheets extending from the fastening means 11. In case there are two proximal or distal flaps, they can be symmetrical, meaning that they have similar shapes and dimensions, or asymmetrical, meaning they can have shapes and dimensions different from each other.

Said two proximal flaps 4b are fixed to the swab head 3 at one end by the fastening means 11 and have each a free margin opposite the distal end side of the respective sheet of fabric. During use, the two proximal flaps 4b can transition from an open state, wherein their two free margins get away from each other to a closed state, wherein their two free margins touch or are very close to each other. Said two proximal flaps 4b each has an inner face, which is the surface of the flap positioned toward the other flap when in closed state, and an opposite outer face, which is the surface of the flaps positioned toward the exterior of the sampling cloth 4 when in closed state.

A sampling cloth 4 provided with such proximal flaps 4b can efficiently sample specimens, because, during insertion of the swab kit into the bodily cavity, the proximal flaps 4b transition to said open state, by the friction with the walls of the bodily cavity. This allows the specimens to be collected mainly on the inner faces of the proximal flaps 4b which are often positioned in the bodily cavity, when the swab kit is fully inserted, at the most important area for sampling, which is usually in the vicinity of the internal opening of the bodily cavity. During removal from the bodily cavity, the proximal flaps 4b transition to the closed state, thus catching the specimens between the flaps, on their inner faces and protecting them from the contact with the cavity's walls or with the exterior. This ensures that a sufficient amount of specimens are successfully sampled and kept on the inner faces of the flaps 4b, which are not lost because only the external faces of the proximal flaps 4b and rest of the sampling cloth 4 are wiped due to friction with the walls of the bodily cavity during removal.

Said one or two distal flaps 4a are fixed to the swab head 3 at one end by the fastening means 11 and have each a free margin opposite to the proximal end of the respective sheet of fabric. During use, the one or two distal flaps 4a can transition from an open state, wherein their free margins are unfolded along the longitudinal axis of the swab head in continuation of said sheet of fabric from said fastening means 11 to a closed state, wherein their free margins fold over the rest of the sheet of fabric. Said one or two distal flaps 4a each has an outer face, which is the surface of the flap positioned toward the swab head, and an opposite inner face.

A sampling cloth 4 provided with at least one such distal flap 4a can efficiently sample specimens, because, during insertion of the swab kit into the bodily cavity, the distal flaps 4a transition to said open state, by the friction with the walls of the bodily cavity. This allows the specimens to be collected mainly on the inner faces of the distal flaps 4a. During removal from the bodily cavity, the distal flaps 4a transition to the closed state, thus catching the specimens in the area between the flap and the fabric sheet, on their inner faces and protecting them from the contact with the cavity's walls or with the exterior. This ensures that a sufficient amount of specimens are successfully sampled and kept on the inner faces of the flaps 4a, which are not lost because only the outer faces of the distal flaps 4a are wiped due to friction with the walls of the bodily cavity during removal.

According to another aspect, the present invention relates to a swab kit comprising:
- a swab applicator having an elongated swab head and a swab rod,
- a low-absorbent, flexible sampling cloth fastened to said swab head 3 by fastening means, the sampling cloth having a distal end and a proximal end, said distal and proximal ends defining an insertion direction (x) of the swab applicator inside a human or animal bodily cavity wherein said proximal end is the end that first enters the bodily cavity and said distal end is the end that last enters the bodily cavity wherein the sampling cloth comprises at least one flap situated at the distal end thereof having a fixed end that is fastened by the fastening means to the swab head and one free end, opposite to the fixed end, that is not attached to the swab head, wherein said flap has a length between the fixed end and the free end of at least 3 mm, more preferably between 3 mm and 10 mm.

The flap according to the present aspect has the same role and may be formed in the same way as a distal flap described above. However, the sampling cloth according to the present aspect may be used together with an applicator having a breakable section as described above or with any applicator for insertion of a sampling cloth in a human or animal bodily cavity.

Yet in a preferred embodiment, the sampling cloth has all the features and characteristics described throughout the present description.

The breakable section 5 of the swab applicator 1 may be placed, in a preferred embodiment of the swab kit in the proximity of the distal end of the sampling cloth 4 (see FIGS. 6a, 6b, 10a, 10d), or preferably partially or completely under the distal end of the sampling cloth 4 (see FIGS. 7a, 7b, 8a, 8b, 9a, 9b). This will ensure that during insertion of the swab kit, the sampled tissue is not damaged due to friction with the swab applicator's surface 1.

The sterilization of the sampling cloth 4 is preferably made using UV light. The sampling cloth 4 shaped substantially in the form of a single sheet of fabric welded on a single exterior surface of the elongated swab head 3 of the swab applicator 1 along its longitudinal axis is preferred because the sterilization is made in only one step and thus, the lead time is reduced by half compared to the sterilization process for the sampling cloth 4 having two sheets of fabric on two exterior surfaces of the elongated swab head 3.

In an alternative embodiment of the invention, the sampling cloth 4 as described above can be used with any type of conventional swab applicator.

The recipient 9 of the swab kit is preferably made of a suitable standard material such as plastic, and has the dimensions adapted to house the entire sampling cloth 4. Said recipient 9 is provided with at least one opening equipped with sealing means. At least one of the openings of said recipient 9 has dimensions sufficient to allow the user of the kit to easily place the sampling cloth 4 inside the recipient 9, preferably without squeezing the cloth 4, which might result in removing part of the collected specimens. Therefore, the dimensions of said opening will depend on the width of the sampling cloth 4. For example, said recipient 9 may be in the form of a plastic jar, vial or tube provided with a thread cap. Optionally, said recipient 9 may contain means for preserving the specimen or further preparing it for a desired subsequent examination, such as saline water, culture medium (for bacterial analysis), KOH solution (for fungal analysis), etc.

Swab Kit Provided with a Sampling Cloth Wound in Turns Around a Swab Rod

In further embodiments, shown in FIGS. 11 and 12, the swab kit according to the invention comprises a swab applicator 1 comprising a swab rod 2 having an extremity E, and a sampling cloth 4 made of a low-absorbent flexible fabric; the sampling cloth 4 is fixed to and wound in overlapping turns T around the swab rod 2, over a swab rod end region neighboring the extremity E, in such a manner that at least an edge portion of the sampling cloth 4 overtops the extremity E by at least 1 mm when measured in a longitudinal direction of the swab rod 2.

The cloth according to the embodiments of FIGS. 11 and 12 is similar to the one described above for the other previous swab kit embodiments, for example with a similar absorbency, flexibility, thickness, basis weight, materials, etc. For example, the sampling cloth 4 may be made of a flexible fabric with an absorbency of 3.5 g/g or less, a thickness of 3 mm or less, preferably 2 mm or less, more preferably 1 mm or less, most preferably 0.6 mm or less, and a basis-weight of approximately 60 g/m$^2$. Said edge portion of the sampling cloth 4 overtops the extremity E preferably by 1 to 10 mm. The sampling cloth is preferably configured as a strip. The extremity E is preferably a rounded extremity.

The wording "wound in overlapping turns" must be interpreted broadly, meaning that the winding has more than one turn and may include full turns as well as fractions of a turn (examples of "turns": 1¼ turns; 2 turns; 3½ turns).

The wording "at least an edge portion of the sampling cloth overtops the extremity E" means that, depending on the embodiment, either only a portion of the edge of the sampling cloth overtops the extremity E, or the entire edge (i.e. the entire length of the edge) of the sampling cloth overtops the extremity E.

The wording "configured as a strip" must be interpreted as a piece of fabric having a substantially rectangular shape with the length at least two times greater than the width.

The term "rounded extremity" must be interpreted broadly, meaning a smooth surface having a shape that significantly reduces the risk of damaging the bodily cavity tissue (unlike, for example, a surface with sharp edges or protuberances). For example, the rounded extremity E may be a hemisphere or a spherical cap.

The dimensions of the rod 2 are adapted to the bodily cavity in which it is desired to be inserted. For example, when designed for the vaginal cavity, the length of the rod 2 is preferably in the range between 120 and 150 mm and the diameter is preferably in the range between 1.5 and 2 mm. The lateral surface of the rod 2 may be cylindrical or may be shaped as a truncated cone with a small slant (less than 5 degrees).

The sampling cloth 4 of the sampling kit has a width preferably in the range between 1 and 60 mm. The swab rod end region over which the sampling cloth 4 is wounded has a length preferably in the range between 5 and 100 mm. Before carrying out the sampling operation, the top surface of the extremity E is not in contact with the sampling cloth 4.

The swab kit may optionally include a recipient adapted to house the entire sampling cloth 4 after the sampling operation has been performed.

FIG. 11*a* shows an embodiment of a swab kit according to the invention, comprising a swab applicator 1 having a "straight" (i.e. having a straight central longitudinal axis) swab rod 2 provided with an extremity E (a rounded extremity in this particular case). A sampling cloth 4 (configured as a strip) made of a low-absorbent flexible fabric is fixed to and wound in overlapping turns T around the swab rod 2, over a swab rod end region neighboring the extremity E, such that the entire top edge of the sampling cloth 4 overtops the extremity E.

The sampling cloth 4 is fixed to the swab rod 2 in a first fixing region R1 (not visible in FIG. 11*a*) by any known means, preferably by welding (in one point, or in several points, or in line) an end F of the sampling cloth 4 to the swab rod 2.

The other end of the sampling cloth 4 is secured to the swab rod 2 by fixing the last turn to the penultimate turn in a second fixing region R2. In FIG. 11*a* the second fixing region R2 is a line welding, but any other suitable fixing means may be used. The turns T overlap each other completely, meaning that the width of the whole winding is substantially equal to the width of the sampling cloth 4. In other words, the turns T are arranged at said edge that overtops the extremity E at the same level, with a pitch value equal to zero.

FIG. 11*b* shows a view from above of the swab kit from FIG. 11*a*, wherein a sampling cloth end F, that is welded to the swab rod 2 in the first fixing region R1, is also visible.

FIG. 11*c* shows a detail of the top region of the swab kit from FIG. 11*a*, but viewed from a different angle, wherein it is clearly shown that the entire top edge of the sampling cloth 4 overtops the extremity E.

One beneficial effect of the sampling kit of FIGS. 11*a*-11*c* is that it enables a normal user, in addition to a trained person, to harvest much more sampling specimens than by using a conventional sampling kit. This sampling kit embodiment according to the invention was proven to be particularly efficient when sampling DNA.

Said effect is due to the following operation of the swab kit: initially, the turns T of the sampling cloth 4 overlap completely. Then, when introducing the applicator 1 inside the bodily cavity (in order to carry out the sampling operation), due to the friction between the sampling cloth 4 and the bodily cavity walls, the turns T slide in respect of each other in a direction opposite to the extremity E. Then, when the applicator 1 is extracted from the bodily cavity (after the sampling of the specimens was carried out), due to the friction between the sampling cloth 4 and the bodily cavity walls, the turns T slide in respect of each other, in a direction towards the extremity E, and may regain their initial position (i.e. overlap completely), which ensures that the harvested specimens are securely entrapped between the turns T. That provides the beneficial effects of avoiding the situation when a large amount of specimens remain stuck to the bodily cavity walls, and of avoiding contamination of the harvested specimens (due to the fact that the specimens situated on a turn T of the sampling cloth 4 are covered/protected by the subsequent turn T of the sampling cloth 4).

Another surprising beneficial effect of the sampling kit of FIGS. 11a-11c is that much less mucus (comparing with a conventional sampling kit) is harvested together with the sampling specimens. The less mucus harvested, the better the specimens analysis quality.

Another beneficial effect of the sampling kit of FIGS. 11a-11c is that the top of the applicator 1 is morphologically adaptable to the bodily cavity, thus reducing the risk of damaging the bodily cavity tissue and enhancing the comfort of the subject.

FIG. 12a shows an embodiment of a swab kit according to the invention that differs in respect to embodiment of FIGS. 11a-11c is that the turns T of the sampling cloth 4 are arranged in a spiral. The term "spiral" does not refer to a planar spiral as defined in the mathematical field (namely in geometry), but must be interpreted as in the medical field of bandaging (for example: a spiral bandage applied to the arm or to the leg), approximating a helix. The pitch value of the spiral, measured in the longitudinal direction of the rod 2, is at least 1 mm, preferably between 1 and 20 mm.
The spiral starts with the innermost turn (considered "the first" turn) an ends with the outermost turn (considered "the last" turn), in the direction from the extremity E towards the rod extremity opposed to the extremity E. This spiral feature is a very important one, because it facilitates the entrapment of the sampling specimens between the turns T.
In case the spiral would have a direction opposite to the one mentioned above, only a negligible amount of sampling specimens could be entrapped between the turns T.

FIG. 12b shows a view from above of the swab kit from FIG. 12a, wherein a sampling cloth end F, that is welded to the swab rod 2 in the first fixing region R1, is also visible.

FIG. 12c shows a detail of the top region of the swab kit from FIG. 12a, but viewed from a different angle, wherein it is clearly shown that a top edge portion of the sampling cloth 4 overtops the extremity E.

The sampling kit of FIGS. 12a-12c has a similar advantage of the embodiment shown in FIGS. 11a-11c, i.e. it enables a normal user, in addition to a trained person, to harvest much more sampling specimens than by using a traditional sampling kit, due to the fact that the sampling specimens are entrapped between two consecutive turns T of the cloth 4 as well as between the first turn of the sampling cloth 4 and the swab rod 2.

A further advantage of the sampling kit of FIGS. 12a-12c is that the amount of sampling specimens harvested is even bigger than in the case of the embodiment of FIGS. 11a-11c. This effect is due to the fact that the spiral turns provide an area of entrapment of the specimens that is much greater than in the case when the turns overlap completely. This effect is also due to the fact that the turns T may slide in respect of each other, thus modifying the pitch of the spiral.

The explanation is the following: initially, the turns T of the spiral have a starting pitch value. Then, when introducing the applicator 1 inside the bodily cavity (in order to carry out the sampling operation), due to the friction between the sampling cloth 4 and the bodily cavity walls, the turns T slide in respect of each other in a direction opposite to the extremity E, thus increasing the pitch of the spiral (comparing to the starting pitch value), and thus increasing the specimens area of entrapment. Then, when the applicator 1 is extracted from the bodily cavity, due to the friction between the sampling cloth 4 and the bodily cavity walls, the turns T slide in respect of each other, in a direction towards the extremity E, thus decreasing the pitch of the spiral (comparing to the starting pitch value). Said decreasing of the pitch value ensures that the harvested specimens are securely entrapped between the turns T. That provides the beneficial effects of avoiding the situation when a large amount of specimens remain stuck to the bodily cavity walls, and of avoiding contamination of the harvested specimens (due to the fact that the specimens situated on a turn T of the sampling cloth 4 are covered/protected by the subsequent turn T of the sampling cloth 4).

A further advantage of the sampling kit of FIGS. 12a-12c is that, when the applicator 1 is inserted into the bodily cavity, the portion of the sampling cloth overtopping the extremity E will come into contact with and cover said extremity E, further reducing the risk of damaging the bodily cavity tissue and enhancing the comfort of the subject.

In both embodiments of FIGS. 11 and 12, instead of a straight (i.e. straight central longitudinal axis) swab rod 2, a bent swab rod 2 may be used (not shown in the figures). Such a bent swab rod 2 comprises a first rod segment that includes the swab rod end region covered by the sampling cloth 4, and a second remaining rod segment (not covered by the sampling cloth 4), wherein the angle between said two rod segments is preferably in the range between 158 and 171 degrees.

A swab applicator 1 having a bent swab rod 2 provides the advantage that, due to the eccentric rotation of the applicator 1 (implicitly of the swab cloth 4) inside the bodily cavity, a thorough contact along the entire circumference of the bodily cavity is achieved, thus leading to a precise and quantitative sampling of specimens.

In both embodiments of FIGS. 11 and 12, irrespective of the swab rod shape (either straight or bent), the swab rod 2 may have a breakable section arranged such that the first fixing region R1 is situated between the extremity E and said breakable section. Said breakable section is preferably situated at a distance in the range 1 to 100 mm from the first fixing region R1. In some embodiments, the breakable section may be entirely covered by the sampling cloth 4, or may be partially covered by the sampling cloth 4, or may not at all be covered by the sampling cloth 4.
The breakable section is configured to break upon exertion of a force and may be designed for example as described in paragraphs [0023]÷[0039] and in FIGS. 1-10, or may have any other suitable design.

In case of swab kit embodiments having a bent swab rod 2 and provided with a breakable section, it is particularly advantageous to arrange said breakable section at the intersection of said first and second segments of the swab rod 2. That ensures less effort (i.e. less torque applied) for the user when breaking the swab rod, as well as a more effective manufacturing process of the swab kit (particularly of the swab rod).

Process of Manufacturing a Swab Kit Having the Sampling Cloth Wound in Turns Around a Swab Rod All the swab kits embodiments described above in paragraphs [0069]=[0089] can be manufactured using a manufacturing process according to the invention, comprising the steps of:

a) providing a swab applicator 1 comprising a swab rod 2 having an extremity E; the swab rod 2 of the applicator 1 may be of any of the kinds mentioned in above paragraphs [0069]-[0089];

b) providing a rolled sampling cloth 4 made of a low-absorbent flexible fabric;

c) fixing a free end F of the rolled sampling cloth 4 to the swab rod 2 in a first fixing region R1;

d) wounding the rolled sampling cloth 4 in overlapping turns T around the swab rod 2, over a swab rod end region neighboring the extremity E, in such a manner that an edge portion of the rolled sampling cloth 4 overtops the extremity E by at least 1 mm, preferably between 1 to 10 mm, when measured in a longitudinal direction of the swab rod 2;

e) fixing a last turn T to a penultimate turn T in a second fixing region R2 such that the turns (T) of the sampling cloth (4) are slidable in respect of each other;

f) cutting the rolled sampling cloth 4, over its entire width, after the second fixing region R2.

The advantage of the manufacturing process according to the invention is that it is extremely simple (i.e. comprises only a few steps and needs only conventional equipment) thus efficient and inexpensive.

The manufacturing process steps according to the invention will be better understood from FIGS. 13*a*-13*e* and FIGS. 14*a*-14*e* that correspond to the manufacturing processes of the embodiments from FIGS. 11*a*-11*c* and respectively 12*a*-12*c*.

Figure 13A:
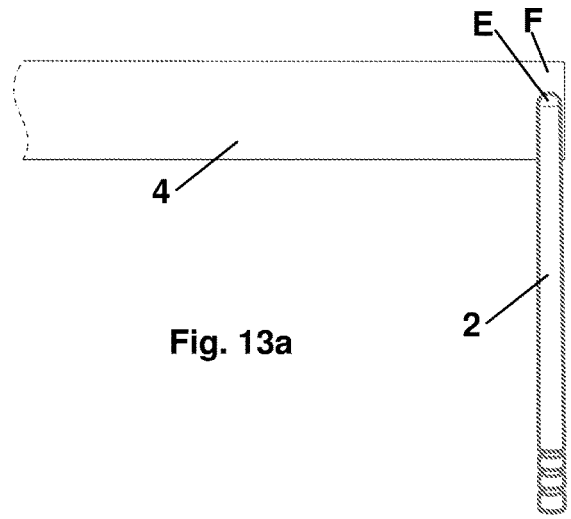
FIGS. 13a-13e show the process steps of manufacturing the swab kit embodiment of FIGS. 11a-11c.

FIG. 13*a* and FIG. 14*a* display the process steps a) and b): providing a swab applicator comprising a swab rod 2 having an extremity E (a rounded extremity in these particular cases) as well as providing a sampling cloth 4 (in these particular cases, the sampling cloth 4 is configured as a strip). For simplicity reason, the roll of sampling cloth is not shown in the figures, only the last portion (depicted unfolded) of the roll is represented.

Figure 13B:
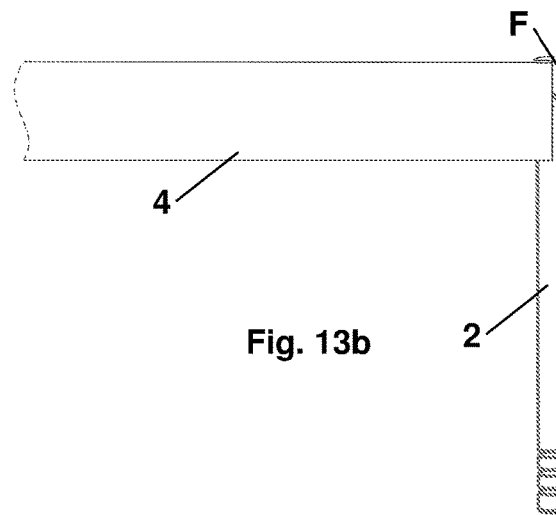

FIG. 13*b* and FIG. 14*b* display the process step c): fixing a free end F of the rolled sampling cloth 4 to the swab rod 2 in a first fixing region. For simplicity reason and because it is concealed by the sampling cloth 4, the first fixing region reference number (i.e. R1) is not present.

Figure 13C:
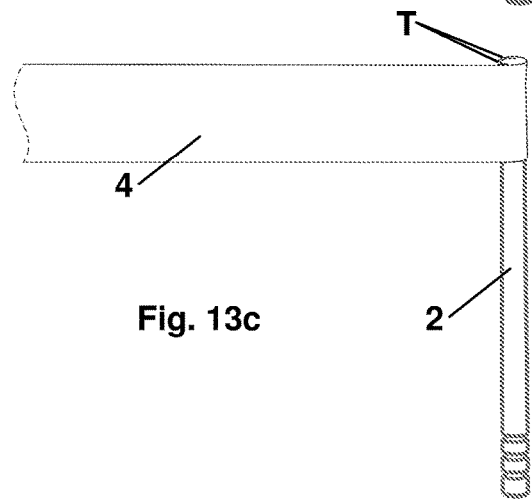

FIG. 13*c* and FIG. 14*c* display the process step d): wounding the rolled sampling cloth 4 around the swab rod 2, over a swab rod end region neighboring the extremity E, in such a manner that an edge portion of the rolled sampling cloth 4 overtops the extremity E by a certain distance (in practice said distance is preferably at least 1 mm, when measured in a longitudinal direction of the swab rod 2). It is preferable that the innermost turn T to be formed by folding the sampling cloth 4 over the free end F. In other words, a first sector of the innermost turn T to overlap said free end F. This arrangement is best visualized in FIGS. 11*b* and 12*b*: immediately after the fixing region R1, the innermost turn is formed by folding the sampling cloth 4 over the free end F.

Figure 13D:
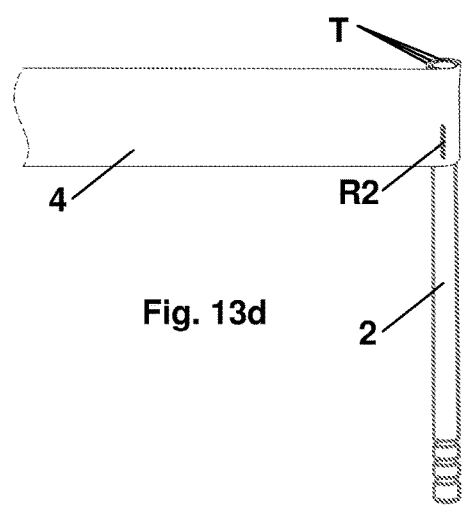

FIG. 13*d* and FIG. 14*d* display the process step e): fixing the last turn to the penultimate turn in a second fixing region R2.

Figure 13E:
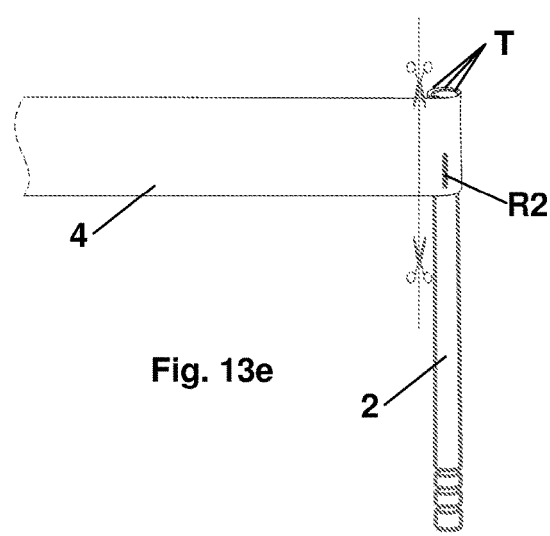

FIG. 13*e* and FIG. 14*e* display the process step f): cutting the rolled sampling cloth 4, over its entire width, after the second fixing region R2.

The remaining of the roll of sampling cloth 4 can then be used with further swab rods for manufacturing further swab kits, using the same above-mentioned process.

The wounding of the rolled sampling cloth 4 in overlapping turns T around the swab rod 2 carried out in step d) may be performed:

either by revolving the rolled sampling cloth 4 around the swab rod 2, while the swab rod 2 is kept immobile, or by rotating the swab rod 2 about its longitudinal axis, while keeping the rolled sampling cloth 4 immobile.

According to the manufacturing process, the turns T of the sampling cloth 4 may overlap each other completely (i.e. are arranged at said edge that overtops the extremity E, at the same level, with a pitch value equal to zero, as in FIGS. 13*d*-13*e*) or may be arranged in a spiral (as in FIGS. 14*c*-14*e*) with a pitch value of at least 1 mm, preferably in the range between 1 and 20 mm, the direction from an innermost turn of the spiral to an outermost turn of the spiral being from the extremity E towards the rod 2 extremity opposed to the extremity E.

According to the manufacturing process, the swab rod 2 may have a straight central longitudinal axis (as in FIGS. 13 and 14) or may be bent (not shown in figures) as previously described in paragraph [0086].

According to the manufacturing process, the swab rod 2 may have a breakable section arranged as previously described in paragraphs and [0089].

In order to ensure the obtaining of a disinfected swab kit, the manufacturing process according to the invention may further comprise the following steps:

before step c), the steps:

b1) disinfection of the outer surface of the swab applicator 1 (implicitly of the swab rod 2);

b2) un-rolling the sampling cloth 4 over a length portion that will be wound around the swab rod 2 in step d);

b3) disinfection of both surfaces of said un-rolled sampling cloth 4 portion. and after step f), the step:

g) disinfection of all the outer surfaces of the swab kit obtained after step f).

The risk of contamination of the swab kit is virtually excluded because the manufacturing process is carried out automatically on machines, no human being present in close proximity thereof.

Each disinfected swab kit can then be introduced in a sterile sealed bag. Then the sterile sealed bag can be put inside a commercially suitable box.

Although the invention has been described in connection with particular illustrative embodiments, it will be clear that it is not, in any way, limited to these embodiments and that it covers all the technical equivalents of the means described and their combinations, insofar as the same function is achieved.

The invention claimed is:

1. Process of manufacturing a swab kit for sampling specimens from humans or animals, comprising the steps of:
   a) providing a swab applicator (1) comprising a swab rod (2) having an extremity (E);
   b) providing a rolled sampling cloth (4) made of a flexible fabric having an absorbency of 3.5 g/g or less;
   c) fixing a free end (F) of the rolled sampling cloth (4) to the swab rod (2) in a first fixing region (R1);
   d) winding the rolled sampling cloth (4) in overlapping turns (T) around the swab rod (2), over a swab rod end region neighboring the extremity (E), in such a manner that:

an edge portion of the rolled sampling cloth (4) overtops the extremity (E) by at least 1 mm, when measured in a longitudinal direction of the swab rod (2), and the turns (T) of the sampling cloth (4) are arranged in a spiral with a pitch value of at least 1 mm, and wherein the direction from an innermost turn of the spiral to an outermost turn of the spiral being from the extremity (E) towards a rod (2) extremity opposed to the extremity (E)

e) fixing a last turn (T) to a penultimate turn (T) in a second fixing region (R2), such that the turns (T) of the sampling cloth (4) are slidable in respect of each other; and f) cutting the rolled sampling cloth (4), over its entire width, after the second fixing region (R2);

and wherein the process further comprises, before step c), the steps:

b1) disinfecting the outer surface of the swab applicator (1);

b2) un-rolling the sampling cloth (4) over a length portion that will be wound around the swab rod (2) in step d);

b3) disinfecting both surfaces of said un-rolled sampling cloth (4) portion. and after step f), the step:

g) disinfecting all the outer surfaces of the swab kit obtained after step f).

2. Process according to claim 1, wherein, in the winding step d), an innermost turn (T) is formed by folding the sampling cloth (4) over the free end (F).

3. Process according to claim 1, wherein the winding of the rolled sampling cloth (4) in overlapping turns (T) around the swab rod (2) carried out in step d) is performed:

either by revolving the rolled sampling cloth (4) around the swab rod (2), while the swab rod (2) is kept immobile, or by rotating the swab rod (2) about its longitudinal axis, while keeping the rolled sampling cloth (4) immobile.

4. Process according to claim 1, wherein the swab rod (2) has a straight central longitudinal axis.

5. Process according to claim 1, wherein a first segment of the swab rod (2) that includes the swab rod end region to be covered by the sampling cloth (4), is bent in respect to a second remaining segment of the swab rod (2) at an angle in the range between 158 and 171 degrees.

6. Process according to claim 5, wherein the swab rod (2) has a breakable section arranged such that the first fixing region (R1) is situated between the extremity (E) and said breakable section.

7. Process according to claim 6, wherein said breakable section is arranged at an intersection of said first and second segments of the swab rod (2).

8. Process according to claim 1, wherein the sampling cloth (4) is made of a fabric with a thickness of 3 mm or less.

9. Process according to claim 1, wherein the sampling cloth (4) is made of a fabric having a basis-weight of 60 g/m$^2$.

* * * * *